US010842804B2

(12) United States Patent
Chang et al.

(10) Patent No.: US 10,842,804 B2
(45) Date of Patent: Nov. 24, 2020

(54) MUPARFOSTAT FOR USE IN TREATING PATIENTS WITH HEPATITIS VIRUS-RELATED HEPATOCELLULAR CARCINOMA AFTER SURGICAL RESECTION

(71) Applicant: MEDIGEN BIOTECHNOLOGY CORP., Taipei (TW)

(72) Inventors: Stanley Chang, Taipei (TW); Kuan-Lang Lai, Taipei (TW)

(73) Assignee: Medigen Biotechnology Corporation, Taipei (TW)

( * ) Notice: Subject to any disclaimer, the term of this patent is extended or adjusted under 35 U.S.C. 154(b) by 0 days.

(21) Appl. No.: 15/892,343

(22) Filed: Feb. 8, 2018

(65) Prior Publication Data

US 2018/0250317 A1 Sep. 6, 2018

Related U.S. Application Data

(60) Provisional application No. 62/465,170, filed on Mar. 1, 2017, provisional application No. 62/504,552, filed on May 11, 2017, provisional application No. 62/551,770, filed on Aug. 29, 2017.

(51) Int. Cl.
*A61K 31/702* (2006.01)
*A61P 35/00* (2006.01)

(52) U.S. Cl.
CPC ............ *A61K 31/702* (2013.01); *A61P 35/00* (2018.01)

(58) Field of Classification Search
CPC ..... A61K 31/702; A61K 31/7024; A61P 1/16; A61P 35/00
See application file for complete search history.

(56) References Cited

U.S. PATENT DOCUMENTS

2014/0135282 A1 5/2014 Chang et al.

OTHER PUBLICATIONS

Liu, C. et al "Adjuvant heparanase inhibitor PI-88 therapy . . . " World J. Gastroenterol., vol. 20, issue 32, pp. 11384-11393. (Year: 2014).*

Hong, Y. et al "Immunotherapy for hepatocellular carcinoma . . . " World J. Hepatol., vol. 7, issue 7, pp. 980-992. (Year: 2015).*

Gandhi, N. et al "Heparin/heparan sulphate-based drugs" Drug Discov. Today, vol. 15, No. 23/24, pp. 1058-1069. (Year: 2010).*

Lim, K. et al "Microvascular invastion is a better predictor of tumor recurrence . . . " Ann. Surg., vol. 254, No. 1, pp. 108-113. (Year: 2011).*

Du Hui Rong; "PI-88 is effective against sub-ethnic groups Experts recommend tha MEDIGEN BIOTECH CORP. publish the results of the trail in medical annual conferences and journals" Feb. 17, 2017 Published online http://www.chinatimes.com/realtimenews/20170228002402-260410, retrieved Feb. 17, 2017 [Translation enclosed].

Wang et al., "Relationship Between Serum Heparanase and Microscopic Venous Invasion in Patients With Hepatocellular Carcinoma," 2010. Am J Clin Pathol, 134:242-248.

Liu et al., "Heparanase inhibitor PI-88 as adjuvant therapy for hepatocellular carcinoma after curative resection: A randomized phase II trial for safety and optimal dosage," 2009. Journal of Hepatology, 50(5):958-968.

English Translation of Notice of Allowance dated Mar. 31, 2020 from Taiwan Application No. 107106359, a foreign corresponding application to U.S. Appl. No. 15/892,343, 7 pages, and the original Notice of Allowance.

English Translation of Office Action dated Aug. 23, 2019 from Taiwan Application No. 107106359, a foreign corresponding application to U.S. Appl. No. 15/892,343, 7 pages, and the original Office Action.

Translated Japanese Office Action dated Jul. 7, 2020, in Japanese Application No. JP 2019-547371, a foreign corresponding application of U.S. Appl. No. 15/892,343, 8 pages.

Waller, Lisa P. et al, "Hepatocellular carcinoma: A comprehensive review," Nov. 2015. World Journal of Hepatology, 7(26): 2648-2663.

* cited by examiner

*Primary Examiner* — Leigh C Maier
(74) *Attorney, Agent, or Firm* — Lee & Hayes, P.C.

(57) ABSTRACT

Muparfostat for use in reducing intrahepatic tumor recurrence and increasing disease-free survival period in a hepatocellular carcinoma patient with microvascular invasion after curative liver resection, while excluding HCC patients with no vascular invasion and HCC patients with macrovascular invasion, is disclosed. The hepatocellular carcinoma patient with microvascular invasion is identified by examining a resected liver tumor sample from the HCC patient for the presence of microvascular invasion in the sample.

26 Claims, 15 Drawing Sheets

FIG. 6-1

Table 1-1

| Variable | Placebo (n = 261) | Muparfostat (PI-88) (n = 258) | Total (n = 519) | p Value |
|---|---|---|---|---|
| Vascular Invasion | | | | 0.9301 |
| No | 134 (50.0%) | 134 (50.0%) | 268 (51.6%) | |
| Yes | 127 (50.6%) | 124 (49.4%) | 251 (48.4%) | |
| Tumor Size ≥ 5 cm | | | | >0.9999 |
| No | 172 (50.1%) | 171 (49.9%) | 343 (66.1%) | |
| Yes | 89 (50.6%) | 87 (49.4%) | 176 (33.9%) | |
| Stratification in Randomization | | | | 0.9637 |
| No vascular invasion and tumor size < 5 cm | 98 (49.2%) | 101 (50.8%) | 199 (38.3%) | |
| No vascular invasion and tumor size ≥ 5 cm | 36 (52.2%) | 33 (47.8%) | 69 (13.3%) | |
| Vascular invasion and tumor size < 5 cm | 74 (51.4%) | 70 (48.6%) | 144 (27.7%) | |
| Vascular invasion and tumor size ≥ 5 cm | 53 (49.5%) | 54 (50.5%) | 107 (20.6%) | |
| Region | | | | 0.4964 |
| 1. Taiwan | 138 (53.1%) | 122 (46.9%) | 260 (50.1%) | |
| 2. Korea | 96 (47.5%) | 106 (52.5%) | 202 (38.9%) | |
| 3. Hong Kong | 3 (33.3%) | 6 (66.7%) | 9 (1.7%) | |
| 4. China | 24 (50.0%) | 24 (50.0%) | 48 (9.2%) | |
| Age (Years) | 55.08 ± 9.62 | 54.12 ± 10.20 | 54.60 ± 9.91 | 0.4802 |
| Weight (kg) | 65.96 ± 10.63 | 65.83 ± 10.43 | 65.90 ± 10.52 | 0.9713 |
| Height (cm) | 166.48 ± 7.51 | 165.68 ± 7.53 | 166.08 ± 7.52 | 0.2307 |
| Body Mass Index (BMI) | 23.74 ± 3.02 | 23.95 ± 3.26 | 23.84 ± 3.14 | 0.6613 |
| Gender | | | | 0.3664 |
| Female | 44 (45.8%) | 52 (54.2%) | 96 (18.5%) | |
| Male | 217 (51.3%) | 206 (48.7%) | 423 (81.5%) | |
| Hepatitis B | | | | 0.1354 |
| No | 25 (41.0%) | 36 (59.1%) | 61 (11.8%) | |
| Yes | 235 (51.4%) | 222 (48.6%) | 457 (88.2%) | |
| Hepatitis C | | | | 0.2159 |
| No | 227 (51.4%) | 215 (48.6%) | 442 (85.3%) | |
| Yes | 33 (43.4%) | 43 (56.6%) | 76 (14.7%) | |
| Size of the Largest Explanted Tumor (cm) | 4.73 ± 2.89 | 4.73 ± 3.22 | 4.73 ± 3.05 | 0.4482 |
| Size of the Largest Explanted Tumor (Three Categories) | | | | 0.9705 |
| < 5 cm | 172 (50.1%) | 171 (49.9%) | 343 (66.1%) | |
| ≥ 5 cm and < 10 cm | 66 (51.2%) | 63 (48.8%) | 129 (24.9%) | |
| ≥ 10 cm | 23 (48.9%) | 24 (51.1%) | 47 (9.1%) | |
| Vascular Invasion (Three Categories) | | | | 0.8337 |
| Macrovascular invasion | 22 (55.0%) | 18 (45.0%) | 40 (7.7%) | |
| Microvascular invasion only | 105 (49.8%) | 106 (50.2%) | 211 (40.7%) | |
| Absent | 134 (50.0%) | 134 (50.0%) | 268 (51.6%) | |
| Macrovascular Invasion | | | | 0.8775 |
| Absent | 226 (49.7%) | 229 (50.3%) | 455 (87.7%) | |
| Present (Hepatic) | 2 (66.7%) | 1 (33.3%) | 3 (0.6%) | |
| Present (Portal) | 12 (48.0%) | 13 (52.0%) | 25 (4.8%) | |
| Present (Both) | 1 (50.0%) | 1 (50.0%) | 2 (0.4%) | |

FIG. 6-2

Table 1-2

| | | | | |
|---|---|---|---|---|
| Present (Not determined) | 6 (75.0%) | 2 (25.0%) | 8 (1.5%) | |
| Present (Other) | 1 (50.0%) | 1 (50.0%) | 2 (0.4%) | |
| Not assessed | 13 (54.2%) | 11 (45.8%) | 24 (4.6%) | |
| Microvascular Invasion | | | | 0.6618 |
| Absent | 134 (50.0%) | 134 (50.0%) | 268 (51.6%) | |
| Present (Hepatic) | 16 (61.5%) | 10 (38.5%) | 26 (5.0%) | |
| Present (Portal) | 27 (51.9%) | 25 (48.1%) | 52 (10.0%) | |
| Present (Both) | 1 (33.3%) | 2 (66.7%) | 3 (0.6%) | |
| Present (Not determined) | 54 (45.8%) | 64 (54.2%) | 118 (22.7%) | |
| Present (Other) | 29 (55.8%) | 23 (44.2%) | 52 (10.0%) | |
| Number of Tumors | | | | 0.4478 |
| 1 | 235 (51.3%) | 223 (48.7%) | 458 (88.2%) | |
| 2 | 20 (41.7%) | 28 (58.3%) | 48 (9.2%) | |
| ≥ 3 | 6 (46.2%) | 7 (53.8%) | 13 (2.5%) | |
| Tumor Morphology | | | | 0.1616 |
| Uninodular and extension ≤ 50% | 228 (51.7%) | 213 (48.3%) | 441 (85.3%) | |
| Multinodular and extension ≤ 50% | 28 (45.2%) | 34 (54.8%) | 62 (12.0%) | |
| Massive or extension > 50% | 4 (28.6%) | 10 (71.4%) | 14 (2.7%) | |
| Differentiation of Baseline Tumor | | | | 0.0863 |
| Well differentiated | 20 (60.6%) | 13 (39.4%) | 33 (6.4%) | |
| Moderately differentiated | 117 (45.0%) | 143 (55.0%) | 260 (50.2%) | |
| Poorly differentiated | 103 (54.5%) | 86 (45.5%) | 189 (36.5%) | |
| Anaplasia | 21 (58.3%) | 15 (41.7%) | 36 (7.0%) | |
| Surgical Margin of Explanted Tumor(s) ≥ 10 mm | | | | 0.1149 |
| No | 137 (53.7%) | 118 (46.3%) | 255 (49.2%) | |
| Yes | 123 (46.8%) | 140 (53.2%) | 263 (50.8%) | |
| Total CLIP Score | | | | 0.1793 |
| 0 | 171 (53.9%) | 146 (46.1%) | 317 (61.3%) | |
| 1 | 64 (43.5%) | 83 (56.5%) | 147 (28.4%) | |
| 2 | 19 (50.0%) | 19 (50.0%) | 38 (7.4%) | |
| 3 | 3 (30.0%) | 7 (70.0%) | 10 (1.9%) | |
| 4 | 3 (60.0%) | 2 (40.0%) | 5 (1.0 %) | |
| Child-Pugh Stage | | | | >0.9999 |
| A | 258 (50.2%) | 256 (49.8%) | 514 (99.4%) | |
| B | 2 (66.7%) | 1 (33.3%) | 3 (0.6%) | |
| Pre-Operative AFP ≥ 400 ng/ml | | | | 0.4814 |
| No | 197 (51.3%) | 187 (48.7%) | 384 (74.3%) | |
| Yes | 63 (47.4%) | 70 (52.6%) | 133 (25.7%) | |
| Post-Operative AFP > 20 ng/ml | | | | 0.1642 |
| No | 199 (52.2%) | 182 (47.8%) | 381 (73.4%) | |
| Yes | 62 (44.9%) | 76 (55.1%) | 138 (26.6%) | |
| Portal Vein Thrombosis | | | | 0.8770 |
| No | 238 (50.4%) | 234 (49.6%) | 472 (91.3%) | |
| Yes | 22 (48.9%) | 23 (51.1%) | 45 (8.7%) | |
| Pre-Operative Child-Pugh Status | | | | 0.9645 |
| 5 | 242 (50.3%) | 239 (49.7%) | 481 (93.0%) | |
| 6 | 16 (48.5%) | 17 (51.5%) | 33 (6.4%) | |

FIG. 6-3

Table 1-3

| | | | | |
|---|---|---|---|---|
| 7 | 1 (50.0%) | 1 (50.0%) | 2 (0.4%) | |
| 8 | 1 (100%) | 0 (0%) | 1 (0.2%) | |
| Post-Operative Child-Pugh Status | | | | 0.3516 |
| 5 | 207 (51.1%) | 198 (48.9%) | 405 (78.0%) | |
| 6 | 47 (47.0%) | 53 (53.0%) | 100 (19.3%) | |
| 7 | 6 (66.7%) | 3 (33.3%) | 9 (1.7%) | |
| 8 | 1 (20.0%) | 4 (80.0%) | 5 (1.0%) | |
| ECOG Performance Score | | | | >0.9999 |
| 0 | 247 (50.2%) | 245 (49.8%) | 492 (94.8%) | |
| 1 | 14 (51.9%) | 13 (48.1%) | 27 (5.2%) | |
| BCLC Stage | | | | 0.3936 |
| Stage A-Early (A1) | 147 (50.5%) | 144 (49.5%) | 291 (56.1%) | |
| Stage A-Early (A2) | 5 (35.7%) | 9 (64.3%) | 14 (2.7%) | |
| Stage A-Early (A3) | 3 (100%) | 0 (0%) | 3 (0.6%) | |
| Stage A-Early (A4) | 6 (40.0%) | 9 (60.0%) | 15 (2.9%) | |
| Stage B-Intermediate | 75 (49.3%) | 77 (50.7%) | 152 (29.3%) | |
| Stage C-Advanced | 25 (56.8%) | 19 (43.2%) | 44 (8.5%) | |
| TNM Stage | | | | 0.6639 |
| Stage I | 124 (51.6%) | 116 (48.3%) | 240 (46.2%) | |
| Stage II | 84 (47.5%) | 93 (52.5%) | 177 (34.1%) | |
| Stage IIIA | 53 (52.0%) | 49 (48.0%) | 102 (19.7%) | |
| HCC Disease Duration (Weeks) | 2.56 ± 2.06 | 2.93 ± 4.49 | 2.75 ± 3.49 | 0.8066 |
| Curative Resection to First Treatment (Weeks) | 5.32 ± 0.61 | 5.35 ± 0.57 | 5.34 ± 0.59 | 0.8000 |
| Local Disease-Free Survival Event | | | | 0.5222 |
| No | 172 (65.9%) | 163 (63.2%) | 335 (64.5%) | |
| Yes | 89 (34.1%) | 95 (36.8%) | 184 (35.5%) | |
| Central Disease-Free Survival Event (with Biopsy Correction) | | | | 0.2949 |
| No | 187 (71.6%) | 173 (67.1%) | 360 (69.4%) | |
| Yes | 74 (28.4%) | 85 (32.9%) | 159 (30.6%) | |

The sample statistics in this table are presented as mean ± standard deviation for continuous variables and frequency (percentage) for categorical variables. The listed *p* values of statistical tests were calculated using the Wilcoxon rank-sum test for continuous variables and Fisher's exact test for categorical variables.

FIG. 7-1

Table 2-1

| Variable | Placebo (n = 229) | Muparfostat (PI-88) (n = 197) | Total (n = 426) | p Value |
|---|---|---|---|---|
| Vascular Invasion | | | | 0.8463 |
| No | 122 (54.2%) | 103 (45.8%) | 225 (52.8%) | |
| Yes | 107 (53.2%) | 94 (46.8%) | 201 (47.2%) | |
| Tumor Size ≥ 5 cm | | | | >0.9999 |
| No | 155 (53.6%) | 134 (46.4%) | 289 (67.8%) | |
| Yes | 74 (54.0%) | 63 (46.0%) | 137 (32.2%) | |
| Stratification in Randomization | | | | 0.9907 |
| No vascular invasion and tumor size < 5 cm | 87 (53.7%) | 75 (46.3%) | 162 (38.0%) | |
| No vascular invasion and tumor size ≥ 5 cm | 35 (55.6%) | 28 (44.4%) | 63 (14.8%) | |
| Vascular invasion and tumor size < 5 cm | 68 (53.5%) | 59 (46.5%) | 127 (29.8%) | |
| Vascular invasion and tumor size ≥ 5 cm | 39 (52.7%) | 35 (47.3%) | 74 (17.4%) | |
| Region | | | | 0.5367 |
| 1. Taiwan | 122 (56.7%) | 93 (43.3%) | 215 (50.4%) | |
| 2. Korea | 86 (50.0%) | 86 (50.0%) | 172 (40.4%) | |
| 3. Hong Kong | 3 (42.9%) | 4 (57.1%) | 7 (1.6%) | |
| 4. China | 18 (56.3%) | 14 (43.8%) | 32 (7.5%) | |
| Age (Years) | 55.02 ± 9.79 | 53.69 ± 10.34 | 54.41 ± 10.06 | 0.3422 |
| Weight (kg) | 66.19 ± 10.85 | 66.17 ± 10.25 | 66.18 ± 10.57 | 0.8895 |
| Height (cm) | 166.48 ± 7.82 | 166.15 ± 7.54 | 166.33 ± 7.69 | 0.6644 |
| Body Mass Index (BMI) | 23.81 ± 3.05 | 23.94 ± 3.20 | 23.87 ± 3.12 | 0.8199 |
| Gender | | | | 0.1627 |
| Female | 35 (46.1%) | 41 (53.9%) | 76 (17.8%) | |
| Male | 194 (55.4%) | 156 (44.6%) | 350 (82.2%) | |
| Hepatitis B | | | | 0.2155 |
| No | 21 (44.7%) | 26 (55.3%) | 47 (11.0%) | |
| Yes | 208 (54.9%) | 171 (45.1%) | 379 (89.0%) | |
| Hepatitis C | | | | 0.4777 |
| No | 201 (54.5%) | 168 (45.5%) | 369 (86.6%) | |
| Yes | 28 (49.1%) | 29 (50.9%) | 57 (13.4%) | |
| Size of the Largest Explanted Tumor (cm) | 4.54 ± 2.61 | 4.50 ± 2.93 | 4.52 ± 2.76 | 0.4482 |
| Size of the Largest Explanted Tumor (Three Categories) | | | | >0.9999 |
| < 5 cm | 155 (53.6%) | 134 (46.4%) | 289 (67.8%) | |
| ≥ 5 cm and < 10 cm | 58 (54.2%) | 49 (45.8%) | 107 (25.1%) | |
| ≥ 10 cm | 16 (53.3%) | 14 (46.7%) | 30 (7.0%) | |
| Vascular Invasion (Three Categories) | | | | 0.6441 |
| Macrovascular invasion | 16 (61.5%) | 10 (38.5%) | 26 (6.1%) | |
| Microvascular invasion only | 91 (52.0%) | 84 (48.0%) | 175 (41.1%) | |
| Absent | 122 (54.2%) | 103 (45.8%) | 225 (52.8%) | |
| Macrovascular Invasion | | | | 0.8637 |
| Absent | 202 (53.3%) | 177 (46.7%) | 379 (89.0%) | |
| Present (Hepatic) | 1 (50.0%) | 1 (50.0%) | 2 (0.5%) | |
| Present (Portal) | 8 (53.3%) | 7 (46.7%) | 15 (3.5%) | |
| Present (Both) | 1 (50.0%) | 1 (50.0%) | 2 (0.5%) | |

FIG. 7-2

Table 2-2

| | | | | |
|---|---|---|---|---|
| Present (Not determined) | 5 (83.3%) | 1 (16.7%) | 6 (1.4%) | |
| Present (Other) | 1 (100%) | 0 (0%) | 1 (0.2%) | |
| Not assessed | 11 (52.4%) | 10 (47.6%) | 21 (4.9%) | |
| Microvascular Invasion | | | | 0.9824 |
| Absent | 122 (54.2%) | 103 (45.8%) | 225 (52.8%) | |
| Present (Hepatic) | 13 (56.5%) | 10 (43.5%) | 23 (5.4%) | |
| Present (Portal) | 20 (55.6%) | 16 (44.4%) | 36 (8.5%) | |
| Present (Both) | 1 (50.0%) | 1 (50.0%) | 2 (0.5%) | |
| Present (Not determined) | 48 (50.5%) | 47 (49.5%) | 95 (22.3%) | |
| Present (Other) | 25 (55.6%) | 20 (44.4%) | 45 (10.6%) | |
| Number of Tumors | | | | 0.2216 |
| 1 | 208 (55.2%) | 169 (44.8%) | 377 (88.5%) | |
| 2 | 15 (40.5%) | 22 (59.5%) | 37 (8.7%) | |
| ≥ 3 | 6 (50.0%) | 6 (50.0%) | 12 (2.8%) | |
| Tumor Morphology | | | | 0.2818 |
| Uninodular and extension ≤ 50% | 203 (55.0%) | 166 (45.0%) | 369 (86.6%) | |
| Multinodular and extension ≤ 50% | 24 (48.0%) | 26 (52.0%) | 50 (11.7%) | |
| Massive or extension > 50% | 2 (28.6%) | 5 (71.4%) | 7 (1.6%) | |
| Differentiation of Baseline Tumor | | | | 0.0755 |
| Well differentiated | 19 (67.9%) | 9 (32.1%) | 28 (6.6%) | |
| Moderately differentiated | 101 (47.9%) | 110 (52.1%) | 211 (49.5%) | |
| Poorly differentiated | 91 (57.6%) | 67 (42.4%) | 158 (37.1%) | |
| Anaplasia | 18 (62.1%) | 11 (37.9%) | 29 (6.8%) | |
| Surgical Margin of Explanted Tumor(s) ≥ 10 mm | | | | 0.0115 |
| No | 124 (60.2%) | 82 (39.8%) | 206 (48.4%) | |
| Yes | 105 (47.7%) | 115 (52.3%) | 220 (51.6%) | |
| Total CLIP Score | | | | 0.2880 |
| 0 | 155 (57.4%) | 115 (42.6%) | 270 (63.4%) | |
| 1 | 58 (46.8%) | 66 (53.2%) | 124 (29.1%) | |
| 2 | 13 (54.2%) | 11 (45.8%) | 24 (5.6%) | |
| 3 | 2 (40.0%) | 3 (60.0%) | 5 (1.2%) | |
| 4 | 1 (33.3%) | 2 (66.7%) | 3 (0.7%) | |
| Child-Pugh Stage | | | | >0.9999 |
| A | 227 (53.7%) | 196 (46.3%) | 423 (99.3%) | |
| B | 2 (66.7%) | 1 (33.3%) | 3 (0.7%) | |
| Pre-Operative AFP ≥ 400 ng/ml | | | | 0.4230 |
| No | 179 (54.9%) | 147 (45.1%) | 326 (76.5%) | |
| Yes | 50 (50.0%) | 50 (50.0%) | 100 (23.5%) | |
| Post-Operative AFP > 20 ng/ml | | | | 0.2051 |
| No | 182 (55.5%) | 146 (44.5%) | 328 (77.0%) | |
| Yes | 47 (48.0%) | 51 (52.0%) | 98 (23.0%) | |
| Portal Vein Thrombosis | | | | 0.4519 |
| No | 215 (54.3%) | 181 (45.7%) | 396 (93.0%) | |
| Yes | 14 (46.7%) | 16 (53.3%) | 30 (7.0%) | |
| Pre-Operative Child-Pugh Status | | | | 0.8037 |
| 5 | 212 (53.3%) | 186 (46.7%) | 398 (93.4%) | |
| 6 | 15 (60.0%) | 10 (40.0%) | 25 (5.9%) | |

FIG. 7-3

Table 2-3

| | | | | |
|---|---|---|---|---|
| 7 | 1 (50.0%) | 1 (50.0%) | 2 (0.5%) | |
| 8 | 1 (100%) | 0 (0%) | 1 (0.2%) | |
| Post-Operative Child-Pugh Status | | | | 0.1524 |
| 5 | 180 (52.8%) | 161 (47.2%) | 341 (80.0%) | |
| 6 | 43 (55.8%) | 34 (44.2%) | 77 (18.1%) | |
| 7 | 5 (100%) | 0 (0%) | 5 (1.2%) | |
| 8 | 1 (33.3%) | 2 (66.7%) | 3 (0.7%) | |
| ECOG Performance Score | | | | >0.9999 |
| 0 | 218 (53.8%) | 187 (46.2%) | 405 (95.1%) | |
| 1 | 11 (52.4%) | 10 (47.6%) | 21 (4.9%) | |
| BCLC Stage | | | | 0.7407 |
| Stage A-Early (A1) | 135 (53.6%) | 117 (46.4%) | 252 (59.2%) | |
| Stage A-Early (A2) | 5 (62.5%) | 3 (37.5%) | 8 (1.9%) | |
| Stage A-Early (A3) | 2 (100%) | 0 (0%) | 2 (0.5%) | |
| Stage A-Early (A4) | 4 (36.4%) | 7 (63.6%) | 11 (2.6%) | |
| Stage B-Intermediate | 67 (54.0%) | 57 (46.0%) | 124 (29.1%) | |
| Stage C-Advanced | 16 (55.2%) | 13 (44.8%) | 29 (6.8%) | |
| TNM Stage | | | | 0.5849 |
| Stage I | 113 (56.2%) | 88 (43.8%) | 201 (47.2%) | |
| Stage II | 74 (50.7%) | 72 (49.3%) | 146 (34.3%) | |
| Stage IIIA | 42 (53.2%) | 37 (46.8%) | 79 (18.5%) | |
| HCC Disease Duration (Weeks) | 2.53 ± 2.05 | 2.84 ± 4.27 | 2.67 ± 3.27 | 0.6646 |
| Curative Resection to First Treatment (Weeks) | 5.31 ± 0.62 | 5.37 ± 0.57 | 5.34 ± 0.60 | 0.4161 |
| Local Disease-Free Survival Event | | | | 0.6795 |
| No | 156 (68.1%) | 130 (66.0%) | 286 (67.1%) | |
| Yes | 73 (31.9%) | 67 (34.0%) | 140 (32.9%) | |
| Central Disease-Free Survival Event (with Biopsy Correction) | | | | 0.3909 |
| No | 168 (73.4%) | 137 (69.5%) | 305 (71.6%) | |
| Yes | 61 (26.6%) | 60 (30.5%) | 121 (28.4%) | |

The sample statistics in this table are presented as mean ± standard deviation for continuous variables and as frequency (percentage) for categorical variables. The listed *p* values of statistical tests were calculated using the Wilcoxon rank-sum test for continuous variables and Fisher's exact test for categorical variables.

FIG. 8

Table 3[1]

| Covariate | Estimate | Standard Error | $z$ Test | $p$ Value | Hazard Ratio | 95% Confidence Interval |
|---|---|---|---|---|---|---|
| Age (Years) | 0.0199 | 0.0091 | 2.1968 | 0.0280 | 1.0201 | 1.0022—1.0384 |
| Number of Tumors: 1 vs. ≥ 2 | -1.1233 | 0.2240 | -5.5061 | <0.0001 | 0.2913 | 0.1878—0.4519 |
| Differentiation of Baseline Tumor: Anaplasia vs. Well, Moderately, or Poorly Differentiated | 0.9179 | 0.2913 | 3.1512 | 0.0016 | 2.5039 | 1.4148—4.4315 |
| Macrovascular Invasion vs. Microvascular Invasion or Absence | 1.0737 | 0.3204 | 3.3511 | 0.0008 | 2.9262 | 1.5616—5.4831 |
| Size of the Largest Tumor > 3.978 cm in Patients with Microvascular Invasions | 1.0342 | 0.2050 | 5.0441 | <0.0001 | 2.8128 | 1.8820—4.2039 |
| Accumulative Time Since the End of Last Cycle of Muparfostat[2] > 16.461 Weeks[3] in Patients with Microvascular Invasions | -2.0578 | 1.0358 | -1.9867 | 0.0470 | 0.1278 | 0.0168—0.9727 |
| Size of the Largest Tumor > 11.043 cm in Patients without Vascular Invasions | 2.0880 | 0.5216 | 4.0031 | <0.0001 | 8.0687 | 2.9029—22.4277 |
| Accumulative Time of Anti-HBV Drug Use after Randomization minus 28 Days Prior to Each Event Time[2] > 60.376 Weeks[3] in Patients without Vascular Invasions | -1.6412 | 0.7561 | -2.1705 | 0.0300 | 0.1937 | 0.0440—0.8529 |

1. Number of patients = 416, number of events = 121, and number of observations (long form) = 16,536. The adjusted generalized $R^2$ = 0.1877 > 0.15 and concordance = 0.7078 (se = 0.0276) > 0.7 indicated an acceptable fit.
2. The two time-dependent covariates "Accumulative Time From the End of the Last Cycle of Muparfostat" and "Accumulative Time of Anti-HBV Drug Use After Randomization Minus 28 Days Prior to Each Event Time" are defined in the specification.
3. The cutoff value of continuous covariates were estimated by the smoothed effect plots of generalized additive models or the Cox's model with the "p=spline" option in R.

FIG. 9-1

Table 4-1

| MedDRA SOC and Preferred Term | Placebo (n = 260) | | Muparfostat (PI-88) (n = 258) | |
|---|---|---|---|---|
| **At least one treatment-related adverse event** | **51** | **(19.6%)** | **152** | **(58.9%)** |
| **General disorders and administration site conditions** | **12** | **(4.6%)** | **81** | **(31.4%)** |
| Injection site haematoma | 7 | (2.7%) | 33 | (12.8%) |
| Injection site haemorrhage | 0 | (0.0%) | 17 | (6.6%) |
| Injection site pain | 1 | (0.4%) | 12 | (4.7%) |
| Injection site reaction | 3 | (1.2%) | 12 | (4.7%) |
| Fatigue | 2 | (0.8%) | 10 | (3.9%) |
| Asthenia | 0 | (0.0%) | 3 | (1.2%) |
| Injection site pruritus | 0 | (0.0%) | 2 | (0.8%) |
| Chest discomfort | 0 | (0.0%) | 1 | (0.4%) |
| Injection site erythema | 0 | (0.0%) | 1 | (0.4%) |
| Injection site mass | 0 | (0.0%) | 1 | (0.4%) |
| Injection site paraesthesia | 1 | (0.4%) | 1 | (0.4%) |
| Pain | 0 | (0.0%) | 1 | (0.4%) |
| Pitting oedema | 0 | (0.0%) | 1 | (0.4%) |
| Chest pain | 1 | (0.4%) | 0 | (0.0%) |
| **Skin and subcutaneous tissue disorders** | **9** | **(3.5%)** | **69** | **(26.7%)** |
| Alopecia | 4 | (1.5%) | 58 | (22.5%) |
| Rash | 2 | (0.8%) | 8 | (3.1%) |
| Pruritus | 2 | (0.8%) | 7 | (2.7%) |
| Ecchymosis | 0 | (0.0%) | 5 | (1.9%) |
| Purpura | 0 | (0.0%) | 4 | (1.6%) |
| Hair texture abnormal | 0 | (0.0%) | 2 | (0.8%) |
| Urticaria | 0 | (0.0%) | 1 | (0.4%) |
| Acne | 1 | (0.4%) | 0 | (0.0%) |
| **Investigations** | **19** | **(7.3%)** | **62** | **(24.0%)** |
| Platelet count decreased | 10 | (3.8%) | 36 | (14.0%) |
| Neutrophil count decreased | 1 | (0.4%) | 17 | (6.6%) |
| Alanine aminotransferase increased | 6 | (2.3%) | 10 | (3.9%) |
| Aspartate aminotransferase increased | 5 | (1.9%) | 7 | (2.7%) |
| White blood cell count decreased | 3 | (1.2%) | 7 | (2.7%) |
| Monocyte count increased | 0 | (0.0%) | 3 | (1.2%) |
| Blood bilirubin increased | 0 | (0.0%) | 2 | (0.8%) |
| Blood fibrinogen decreased | 2 | (0.8%) | 2 | (0.8%) |
| Alpha 1 foetoprotein increased | 0 | (0.0%) | 1 | (0.4%) |
| Blood albumin decreased | 0 | (0.0%) | 1 | (0.4%) |
| Blood alkaline phosphatase increased | 1 | (0.4%) | 1 | (0.4%) |
| Blood lactate dehydrogenase increased | 1 | (0.4%) | 1 | (0.4%) |
| Gamma-glutamyltransferase increased | 1 | (0.4%) | 1 | (0.4%) |
| International normalized ratio increased | 2 | (0.8%) | 1 | (0.4%) |
| Fibrin D dimer increased | 1 | (0.4%) | 0 | (0.0%) |
| Hepatitis B DNA increased | 1 | (0.4%) | 0 | (0.0%) |
| Prothrombin time prolonged | 1 | (0.4%) | 0 | (0.0%) |
| **Gastrointestinal disorders** | **6** | **(2.3%)** | **16** | **(6.2%)** |
| Nausea | 2 | (0.8%) | 6 | (2.3%) |
| Stomatitis | 1 | (0.4%) | 4 | (1.6%) |
| Abdominal pain upper | 1 | (0.4%) | 2 | (0.8%) |
| Diarrhea | 2 | (0.8%) | 2 | (0.8%) |

FIG. 9-2

Table 4-2

| | | | | |
|---|---|---|---|---|
| Abdominal discomfort | 0 | (0.0%) | 1 | (0.4%) |
| Ascites | 0 | (0.0%) | 1 | (0.4%) |
| Dry mouth | 0 | (0.0%) | 1 | (0.4%) |
| Dyspepsia | 0 | (0.0%) | 1 | (0.4%) |
| Gingival bleeding | 0 | (0.0%) | 1 | (0.4%) |
| Mouth ulceration | 0 | (0.0%) | 1 | (0.4%) |
| Abdominal pain | 1 | (0.4%) | 0 | (0.0%) |
| Vomiting | 1 | (0.4%) | 0 | (0.0%) |
| **Blood and lymphatic system disorders** | **2** | **(0.8%)** | **14** | **(5.4%)** |
| Thrombocytopenia | 1 | (0.4%) | 8 | (3.1%) |
| Neutropenia | 0 | (0.0%) | 5 | (1.9%) |
| Leukopenia | 0 | (0.0%) | 2 | (0.8%) |
| Heparin-induced thrombocytopenia | 0 | (0.0%) | 1 | (0.4%) |
| Anemia | 1 | (0.4%) | 0 | (0.0%) |
| **Nervous system disorders** | **1** | **(0.4%)** | **6** | **(2.3%)** |
| Dizziness | 1 | (0.4%) | 2 | (0.8%) |
| Hypoesthesia | 0 | (0.0%) | 2 | (0.8%) |
| Dysarthria | 0 | (0.0%) | 1 | (0.4%) |
| Headache | 0 | (0.0%) | 1 | (0.4%) |

FIG. 10

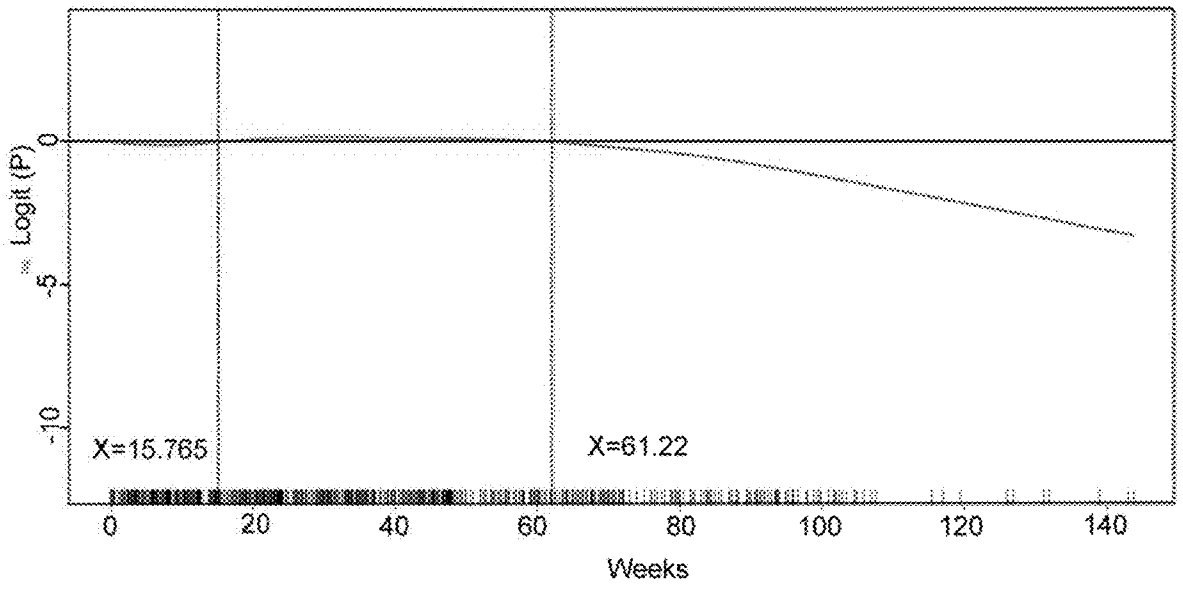

MUPARFOSTAT FOR USE IN TREATING PATIENTS WITH HEPATITIS VIRUS-RELATED HEPATOCELLULAR CARCINOMA AFTER SURGICAL RESECTION

REFERENCE TO RELATED APPLICATION

The present application claims the priority to U.S. Provisional Application Ser. No. 62/465,170, filed Mar. 1, 2017, Ser. No. 62/504,552, filed May 11, 2017, and Ser. No. 62/551,770, filed Aug. 29, 2017, all of which are herein incorporated by reference in their entireties.

FIELD OF THE INVENTION

The present invention relates generally to hepatocellular carcinoma (HCC), and more specifically to methods for increasing disease-free survival rate in HCC patients after surgical resection.

BACKGROUND OF THE INVENTION

The standard treatment for patients with early-stage HCC is local ablation or surgical resection (including liver transplantation). Although surgical resection with curative intent is initially effective, the 5-year disease-free survival (DFS) rate after surgery is as low as 20%-30% because of a high risk of HCC recurrence.

Two unique patterns of recurrence are identified after resection: recurrence derived from residual micrometastases and de novo recurrence owing to persistent carcinogenic changes in the residual liver. Because tumor recurrence and subsequent death are not uncommon after primary HCC resection, several adjuvant modalities aiming to improve patient survival, including systemic chemotherapy, transarterial chemoembolization, interferon α-2b, $^{131}$I-lipiodol, cytokines, sorafenib, and acyclic retinoid, have been used but without success. An effective adjuvant therapy after curative HCC resection remains unavailable and is urgently required.

SUMMARY OF THE INVENTION

In one aspect, the invention relates to a method for reducing intrahepatic tumor recurrence and increasing disease-free survival period, comprising: administering a therapeutically effective amount of muparfostat to a hepatocellular carcinoma (HCC) patient with microvascular invasion after curative liver resection, while excluding HCC patients with no vascular invasion and HCC patients with macrovascular invasion.

In one embodiment, prior to the administering step the method of the invention may further comprises examining a resected liver tumor sample from the HCC patient to identify the presence of microvascular invasion in the sample. In another embodiment, prior to the administering step the method of the invention further comprises assessing whether a liver tumor sample from the HCC patient has microvascular invasion.

The method of the invention may further comprise administering an immune checkpoint inhibitor to the HCC patient with microvascular invasion. The method of the invention may further comprise administering an anticancer agent to the HCC patient with microvascular invasion. The method of the invention may further comprise the step of subjecting the patient to three monthly scheduled surveillance CT scans.

In another embodiment, the muparfostat is the only anticancer agent received by the ICC patient with microvascular invasion after the liver resection.

In another embodiment, the HCC patient with microvascular invasion is non-responsive to anti-hepatitis B virus drug treatment. In another embodiment, the HCC patient with microvascular invasion has hepatitis B virus (HBV)-related HCC or hepatitis C virus (HCV)-related HCC. In another embodiment, the HCC patient with microvascular invasion has one and no more than one single tumor prior to the liver resection. In another embodiment, the HCC patient with microvascular invasion has a postoperative Child-Pugh total score of lower than 8. In another embodiment, the HCC patient with microvascular invasion has a hepatic tumor with a size of smaller or no greater than 10 cm prior to the liver resection. In another embodiment, the HCC patient with microvascular invasion has a well differentiated, or moderately differentiated, or poorly differentiated tumor prior to the liver resection according to a four-tier scale of neoplastic grading. In another embodiment, the HCC patient with microvascular invasion has a body mass index (BMI) of 18.5-35 $kg/m^2$.

In one embodiment, the patient with microvascular invasion is at least 5.2 weeks after the liver resection. In another embodiment, the administering step excludes any HCC patient with microvascular invasion who has an anaplasia hepatic tumor prior to the liver resection.

In one embodiment, the administering step is performed for at least four consecutive days per week for 3 weeks out of every 4 weeks. In another embodiment, the administering step is performed for at least 52 weeks.

In another aspect, the invention relates to a method for treating a hepatocellular carcinoma (HCC) patient after liver resection, comprising: administering a therapeutically effective amount of muparfostat to the HCC patient after the liver resection, wherein the HCC patient has below characteristics: (a) a sign of microvascular invasion; and (b) at least one of the following features: (i) no more than one single tumor prior to the liver resection; (ii) having a postoperative Child-Pugh total score of lower than 8; (iii) having a hepatic tumor with a size of smaller than or no greater than 10 cm prior to the liver resection; and (iv) having a well differentiated, or moderately differentiated, or poorly differentiated tumor prior to the liver resection according to a four-tier scale of neoplastic grading.

In another aspect, the invention relates to a method for treating a hepatocellular carcinoma (HCC) patient with microvascular invasion after liver resection, while excluding hepatocellular carcinoma (HCC) patients with no vascular invasion and HCC patients with macrovascular invasion, said method comprising: administering a therapeutically effective amount of muparbostat to the HCC patient with microvascular invasion after the liver resection.

In one embodiment, the immune checkpoint is selected from the group consisting of PD1, PD-L1, CTLA-4, TIM-3, LAG-3, VISTA, BTLA, TIGIT, LAIR1, CD160, 2B4, TGFR beta, CEACAM-1, CEACAM-3, and CEACAM-5. The immune checkpoint inhibitor may be selected from the group consisting of Pembrolizumab, Nivolumab, Atezolizumab, Avelumab, Durvalumab, and Ipilimumab.

In another aspect, the invention relates to a method of treating a hepatocellular carcinoma (HCC) patient without vascular invasion after liver resection, said method comprising administering a therapeutically effective amount of anti-HBV drug to the patient without vascular invasion. In one embodiment, the step of administering anti-HBV drug to the HCC patient without vascular invasion is performed at least 60 weeks.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

(FIG. 3C) microvascular invasion, and (FIG. 3D) no vascular invasion in the per-protocol analysis based on independent central imaging assessments.

(FIG. 4B) no vascular invasion, and (FIG. 4C) a combination of microvascular invasion and no vascular invasion in the per-protocol analysis based on independent central imaging assessments (overlap of FIGS. 4A and 4B). The "preferable" patients were those with one single tumor (no more than one tumor); postoperative Child-Pugh total score lower than 8; maximum tumor size≤10 cm; well, moderately, or poorly differentiated tumor differentiation; BMI of 18.5-35 kg/m$^2$; time from curative resection to first treatment≥5.2 weeks; and recurrence after 24 weeks from the first treatment.

FIG. 6 (6-1 to 6-3) is a table (Table 1-1 to 1-3) showing a comparison of baseline demographic and clinical characteristics between the placebo and muparfostat (PI-88) groups in the intention-to-treat analysis.

FIG. 7 (7-1 to 7-3) is a table (Table 2-1 to 2-3) showing a comparison of baseline demographic and clinical characteristics between the placebo and muparfostat (PI-88) groups in the per-protocol analysis.

FIG. 8 is a table (Table 3) showing multivariate analysis to identify the predictors of disease-free survival by fitting the Cox's model with time-dependent covariates in patients receiving the placebo or muparfostat (PI-88) in the per-protocol analysis.

FIG. 9 (9-1 to 9-2) is a table (Table 4-1 to 4-2) showing a comparison of treatment-related adverse events (AEs) by the System Organ Class (SOC) and preferred terms between the placebo and muparfostat (PI-88) groups.

FIG. 10 is a graph showing delayed protective effect of anti-HBV drug in a subgroup of patients without vascular invasion after the drug had been administered for a period of 60 weeks.

DETAILED DESCRIPTION OF THE INVENTION

Definitions

Figure 1:
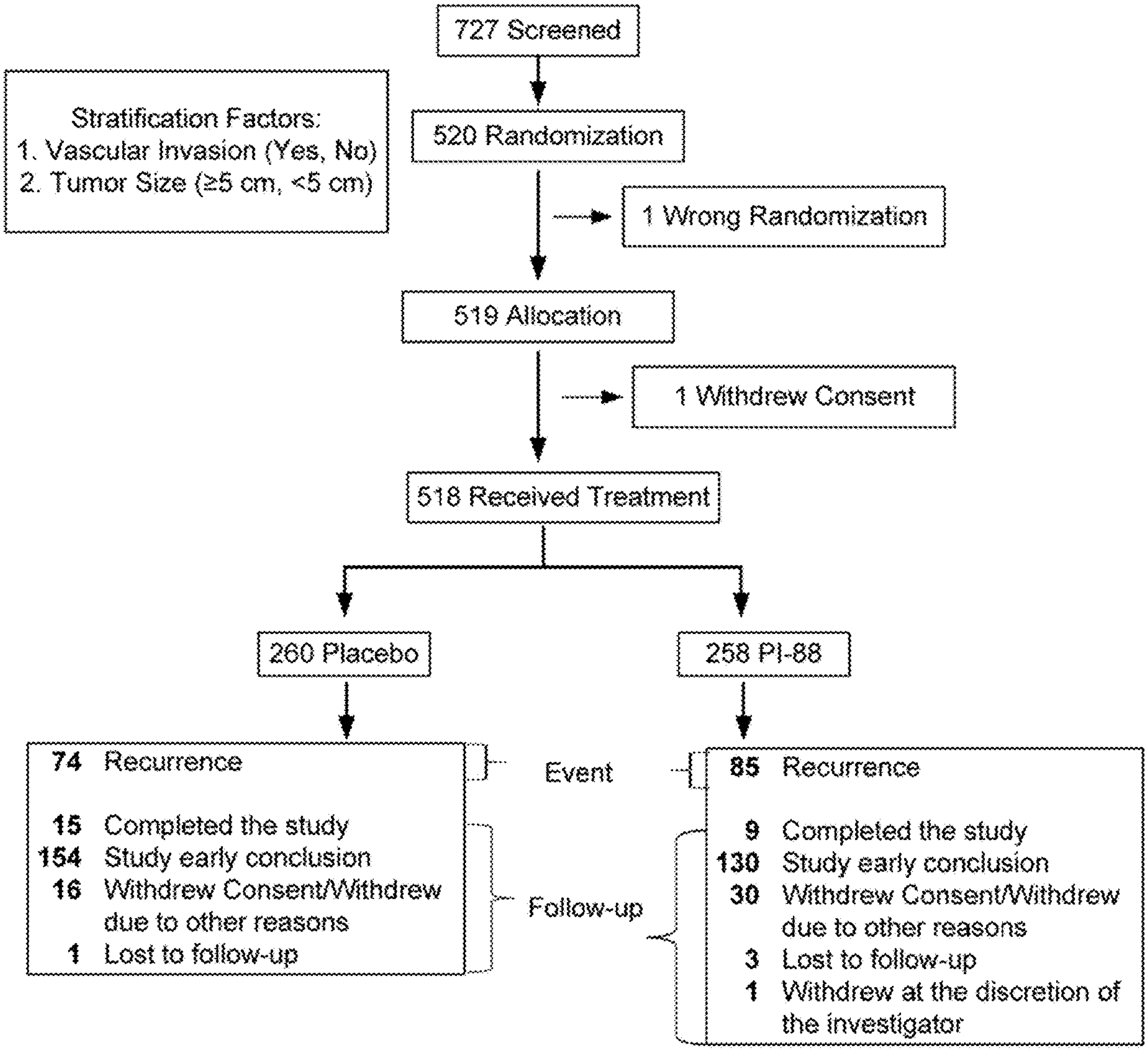
FIG. 1 is a flow diagram of the trial protocol.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "subject" refers to a human or a non-human animal.

The term "treating" or "treatment" refers to administration of an effective amount of a therapeutic agent to a subject in need thereof, who has cancer or infection, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

The term "an effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

The term "baseline event rate" refers to the statistical assumption for the primary endpoint (the DFS) to the treatment and placebo group.

The term "relative risk ratio" refers to the ratio of the probability of an event occurring in a treatment group to the probability of the event occurring in a comparison, placebo group. Relative risk includes two important features: (i) a comparison of risk between two "exposures" puts risks in context, and (ii) "exposure" is ensured by having proper denominators for each group representing the exposure.

The term "censoring" refers to a statistics term. Censoring is a condition in which the value of a measurement or observation is only partially known. Such a situation could occur if the individual withdrew from the study before endpoints achieved. The problem of censored data, in which the observed value of some variable is partially known, is related to the problem of missing data, where the observed value of some variable is unknown.

The terms "PI-88" and "muparfostat" are interchangeable.

The term "OS" refers to overall survival, the percentage of patients alive at a defined time after initiation of the treatment.

The term "DFS" refers to the disease free survival, length of time after treatment that a patient survives with no sign of disease. The most frequent use of DFS as trial endpoint is in the adjuvant setting after definitive surgery. Although overall survival is a conventional endpoint for most adjuvant settings, DFS can be an important endpoint in situations where survival may be prolonged, making a survival endpoint impractical. DFS has been the primary basis of approval for adjuvant therapies. DFS can be a surrogate for clinical benefit or it can provide direct evidence of clinical benefit. This determination is based on the magnitude of the effect, its risk-benefit relationship, and the disease setting.

The Child-Pugh score, also known as Child-Turcotte-Pugh score or Child Criteria, is used to assess the prognosis of chronic liver disease, mainly cirrhosis. It is used to determine the prognosis, as well as the required strength of treatment and the necessity of liver transplantation. The score employs five clinical measures of liver disease. Each measure is scored 1-3, with 3 indicating most severe derangement. See table A below for the score assessment.

TABLE A

| Measure | 1 point | 2 points | 3 points |
|---|---|---|---|
| Total bilirubin, mg/dL | <2 | 2-3 | >3 |
| Serum albumin, g/dL | >3.5 | 2.8-3.5 | <2.8 |
| Prothrombin time, prolongation (s) OR INR | <4.0<br><1.7 | 4.0-6.0<br>1.7-2.3 | >6.0<br>>2.3 |
| Ascites | None | Mild (or suppressed with medication) | Moderate to severe (or refractory) |
| Hepatic encephalopathy | None | Grade I-II | Grade III-IV |

The neoplastic grading is a measure of cell anaplasia (reversion of differentiation) in the sampled tumor and is based on the resemblance of the tumor to the tissue of origin. The grade score (numerical: G1 up to G4) increases with the lack of cellular differentiation—it reflects how much the tumor cells differ from the cells of the normal tissue they have originated from. Tumors may be graded on four-tier, three-tier, or two-tier scales, depending on the institution and the tumor type. In the present invention, the HCC patients were graded by the following four-tier scale: well differentiated (G1), moderately differentiated (G2), poorly differentiated (G3), and anaplasia (G4).

The Kaplan-Meier (KM) survival curve is defined as the probability of surviving in a given length of time while considering time in many small intervals. To estimate the KM, two pieces of data are required for each subject: the "status" at last observation (event/censoring) and the "time" (time to event or time to censoring). The "arm" assigned to the subject will also be required if comparison is to be proceed. The "status" for a subject can only be either event or censoring. Take overall survival as illustration, death is defined as "event" and all the others not dead are "censored".

In the Kaplan-Meier curve, the x-axis is "time", from zero (when observations began) to the last observed time point; the y-axis is the proportion of subjects surviving. At time zero, 100% of the subjects are alive without an event. Each vertical drop indicates an event. In the present invention, the primary efficacy endpoint was DFS period and an event means either tumor occurrence or death. For the research with more than one arm ("arm"), the larger separation between the curves, the greater difference between the arms is demonstrated.

PI-88 (muparfostat) is a novel adjuvant therapy for patients with HCC post resection. In the phase II trial, PI-88 was well tolerated, with favorable safety profiles at 160 mg/day, and demonstrated a promising time-to-recurrence prolongation for patients with HCC after surgical resection, especially in those with hepatitis virus-related HCC. Therefore, in the present phase III, multicenter, randomized clinical trial (RCT), the effect of muparfostat (PI-88), a heparanase inhibitor, on tumor recurrence or death in patients with HBV- or HCV-related HCC after surgical resection was investigated.

Abbreviations

HCC, hepatocellular carcinoma; DFS, disease-free survival; ITT, intention-to-treat; PP, per-protocol; AE, adverse event; HBV, hepatitis B virus; HCV, hepatitis C virus; RCT, randomized controlled trial; HIT, heparin-induced thrombocytopenia; OS, overall survival; SD, standard deviation; HR, hazard ratio; SAE, serious adverse event; ICI, immune checkpoint inhibitor.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Methods of making PI-88 (muparfostat) and the sulfonated phosphomannan components contained in PI-88 were as disclosed in US Patent publication No. 20140135282 and by P. N. Handley et al. (2017) "New structural insights into the oligosaccharide phosphate fraction of *Pichia* (*Hansenula*) *holstii* NRRI. Y2448 phosphomannan" Carbohydrate Research 446-447, pages 68-75. U.S. Patent No. 20140135282 discloses sulfonated phosphomannan components of PI-88 with a chemical structure of formula (I):

(I)

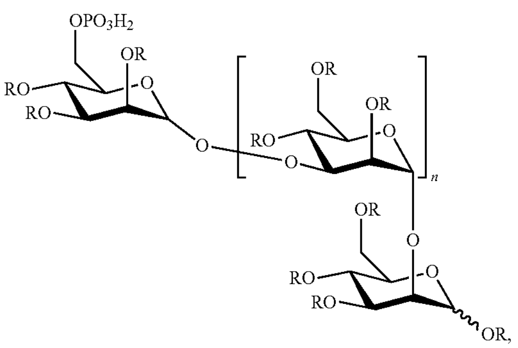

wherein n is an integer of 3, and 3n+7 of the R groups are $SO_3H$.

P. N. Handley et al. discloses sulfonated phosphomannan components of PI-88 with a chemical structure of formula (II) below:

Chart 1. Oligosaccharide structures.

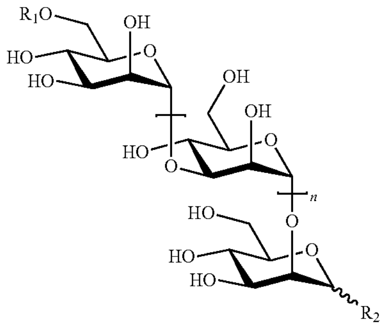

1 n = 4, $R_1 = PO_3^{2-}$, $R_2$ = OH
2 n = 4, $R_1$ = H, $R_2$ = OH
3 n = 3, $R_1 = PO_3^{2-}$, $R_2$ = OH
4 n = 3, $R_1 = PO_3^{2-}$, $R_2$ = β-$NH_2$
5 n = 2, $R_1 = PO_3^{2-}$, $R_2$ = OH
6 n = 2, $R_1 = PO_3^{2-}$, $R_2$ = β-$NH_2$
7 n = 2, $R_1$ = H, $R_2$ = β-$NH_2$
8 n = 1, $R_1 = PO_3^{2-}$, $R_2$ = OH
9 n = 0, $R_1 = PO_3^{2-}$, $R_2$ = OH
10 n = 0, $R_1$ = H, $R_2$ = OH

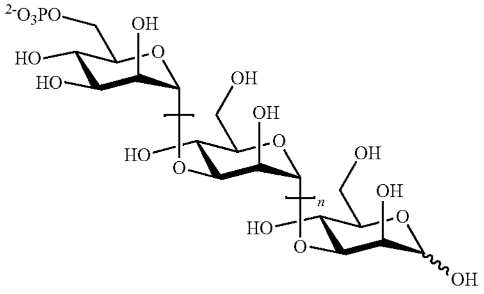

11 n = 3
12 n = 2
13 n = 1
14 n = 0

-continued

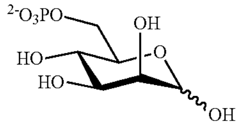

Study Design and Participants

This phase III, international (Taiwan, Korea, China, and Hong Kong), multicenter, double-blind, placebo-controlled RCT of PI-88 as an adjuvant treatment for hepatitis virus-related HCC after surgical resection was initiated in September 2011. The trial is registered at ClinicalTrials.gov (NCT01402908). It was designed to recruit approximately 500 participants to observe 218 events of tumor recurrence or HCC-related death from any cause. The median DFS periods were assumed to be 12 and 18 months for those receiving the placebo and PI-88, respectively. The baseline event rates were 0.693 and 0.462 for those receiving placebo and PI-88, respectively. The relative risk ratio was 0.667 and the censoring rate was 60% with power of 85% and type I error of 0.05.

An interim analysis was conducted after 131 patients developed tumor recurrence or died from any cause. A group sequential design with the Lan-DeMets alpha-spending function was employed in the interim analysis. To assess the effect of PI-88 on the primary endpoint, the two-sided alpha level was set at 0.01806 in the interim analysis and 0.04148 in the final analysis.

All patients provided written, signed, and dated informed consent to participate in this study. The institutional review boards of participating sites approved the study protocol and amendments before the initiation of the RCT. The inclusion criteria were as follows: (1) histologically proven primary HCC with curative resection performed 4-6 weeks prior to randomization (the curative nature of resection is defined by the observations of a clear tumor margin (≥0.1 cm) in postoperative histology results, negative follow-up abdominal and chest contrast-enhanced triphasic spiral computed tomography (CT) scans, and a negative abdominal gadolinium-enhanced magnetic resonance imaging (MRI) scan; patients with evidence of residual lymph node metastases were not enrolled); (2) evidence of HBV or HCV infection; (3) age≥18 years; (4) Eastern Cooperative Oncology Group performance status=0-1; (5) Child-Pugh classification score≤8; and (6) adequate bone marrow and liver function. The exclusion criteria were as follows: (1) diameter of single HCC<2 cm obtained from the most recent hepatectomy; (2) history of immune-mediated thrombocytopenia, other platelet abnormalities, or other hereditary or acquired coagulopathies; laboratory evidence of antiheparin antibodies; or any previous history of having tested positive for antiheparin antibodies; (3) HCC metastasis or prior or coexisting malignant disease; (4) clinically significant nonmalignant diseases (5) history of receiving prior HCC therapy, including chemotherapy and radiotherapy; molecular targeting agents, such as antiangiogenic antibodies or kinase inhibitors; vaccines; transarterial embolization; transarterial chemoembolization; liver transplantation; or surgical resection prior to the most recent hepatectomy; and (6) history of inflammatory bowel disease or any other abnormal bleeding tendency or being at a risk of bleeding due to open wounds or planned surgery.

Randomization

After signing the consent form, the eligibility of each patient was verified according to the enrollment criteria by checking his/her medical records and current disease conditions. Eligible patients were stratified by tumor size (<5 cm vs. ≥5 cm) and vascular invasion (no vs. yes) and then randomized at a ratio of 1:1 within strata to receive PI-88 (160 mg/day) or a placebo by using a centralized interactive web response system (Cenduit Interactive Response Technology; Cenduit, Durham, N.C., USA).

Study Materials

PI-88 was supplied to pharmacies as a sterile lyophilized powder in a glass vial (Par Pharmaceutical, Rochester, Mich., USA) to deliver 160 mg after reconstitution. The placebo was supplied as a sterile, lyophilized powder in a glass vial of identical specifications and appearance to that used for the investigational drug. The principal constituent of the placebo was lactose as a sterile lyophilized powder. The powders and solutions of PI-88 and placebo were identical in appearance to ensure treatment blindness.

Procedures

PI-88 or placebo was administered in a single subcutaneous injection each day for four consecutive days per week for 3 weeks out of every 4 weeks (a cycle with 4-weeks). The days of injection were the same in every administration week. After an initial training period of 1-8 days, participants self-administered the study drug at home. Participants received treatment for up to 52 weeks and were followed until 96 weeks.

If a patient's platelet count fell below $50\times10^9$/liter (<50,000/$mm^3$) or demonstrated a suspicious or unexplained decline to <50% of the baseline value at visit 1, the dosing was suspended immediately, and the most recent blood sample received was immediately sent to the central laboratory for testing the presence of antiheparin antibodies. If the antiheparin antibody test was positive, the participant was asked to permanently discontinue the treatment. A warning was issued to the responsible physician when the antiheparin antibody test result showed a high possibility of heparin-induced thrombocytopenia (HIT). In clinical trial visit 1 means the start of the treatment. The data collected at visit 1 just before the treatment start stands for the baseline data.

Outcome Assessments

The primary efficacy endpoint of this RCT was the DFS period, which was defined as the time from randomization to tumor recurrence or death from any cause. Secondary efficacy endpoints were time to tumor recurrence, tumor recurrence rate, and overall survival (OS). Tumor recurrence was diagnosed according to a radiological algorithm based on three monthly scheduled surveillance CT scans. The radiological algorithm emphasizes a "typical vascular pattern" on CT or MRI. This pattern consists of arterial hypervascularity and early- or late-phase portal/venous "washout." These findings may be demonstrated on a triphasic spiral CT scan or a gadolinium-enhanced MRI scan. Tumor recurrences on CT/MRI scans were assessed independently by a centralized facility according to the radiological algorithm. Liver biopsy was performed to confirm tumor recurrence in case of equivocal findings any time during the diagnostic algorithm.

Central and Local Medical Imaging Assessments

All CT scans and relevant images were forwarded to an independent, centralized CT reading service for retrospective evaluation and central review, in addition to being read contemporaneously at sites. The DFS period was calculated on the basis of both central and local image reading data, with central-read results serving as primary findings and local-read results for validation.

Statistical Analysis

The data were analyzed using the R 3.3.2 software (R Foundation for Statistical Computing, Vienna, Austria). The distributional properties of continuous variables are expressed as mean t standard deviation, categorical variables are presented as frequency and percentage (%), and the survival curves of the DFS period were estimated using the Kaplan-Meier method. Baseline demographic and clinical characteristics were compared between the PI-88 and placebo groups. The safety profiles of PI-88 and the placebo were examined in all randomized patients who received at least one dose of the assigned drug. Efficacy analysis was conducted for the primary endpoint (the DFS period) and secondary endpoints (time to tumor recurrence and OS). Both intention-to-treat (ITT) and per-protocol (PP) analyses were performed.

A. ITT Analysis

The two-sample log-rank test stratified by tumor size (<5 cm vs. ≥5 cm) and vascular invasion (no vs. yes) was conducted to compare the survival curves of the DFS period between the PI-88 and placebo groups. The required proportional hazard assumption between PI-88 and the placebo was verified.

B. Per-Protocol (PP) Analysis

The randomized patients who had taken at least 80% of the required dosage regimen per protocol, did not show recurrence or die within 12 weeks post treatment, did not violate any study entry eligibility criterion, did not receive any excluded concomitant treatment, and were not unblinded during the study period were included in the PP analysis. Because the use of anti-HBV drugs, anti-HCV drugs, and PI-88 in patients might vary over time during the study period, regression analysis was conducted by fitting Cox's proportional hazards models with time-dependent covariates (called the "Cox's model") to estimate the adjusted effects of PI-88, anti-HBV drugs, anti-HCV drugs, and other predictors of the DFS period.

Four time-dependent covariates of the following two types were defined for fitting the Cox's models of disease-free survival (DFS): (1) Accumulative drug days from the first day of taking the drug after randomization to each unique event time of DFS, but without considering the drug usage within the prespecified time lag of 28 days prior to each unique event time of DFS as the "latency period" or "incubation period". The drugs included in this type were: (a) any of the seven anti-hepatitis B virus (HBV) drugs (adefovir, adefovir dipivoxil, entecavir, lamivudine, telbivudine, tenofovir, and tenofovir disoproxil fumarate); (b) any of the five anti-hepatitis C virus (IHCV) drugs (ribavirin, peginterferon, peginterferon alfa-2A, peginterferon alfa-2B, and pegylated interferon alfa-2A); and (c) PI-88. (2) Accumulative elapsed days from the last day of PI-88 use to each unique event time of DFS to examine the "latency effect" or "delayed effect" of PI-88. Technically, we used the "counting process style of input" to reconstruct the original wide-form PP data into long-form PP data for DFS. At each ordered event time of DFS, we computed the values of the aforementioned four time-dependent covariates for all patients at risk in the long-form PP data. Then, we fitted the Cox's model of DFS with all relevant fixed and time-dependent covariates to the derived long-form PP data.

To ensure satisfactory quality of the analysis result, the model-fitting techniques for (1) variable selection, (2) goodness-of-fit (GOF) assessment, and (3) regression diagnostics and remedies were used in our regression analysis. The stepwise variable selection procedure (with iterations between the forward and backward steps) was applied to obtain an optimal candidate for the final Cox's model. All the univariate significant and nonsignificant relevant covariates (Table 2) and some of their interaction terms were added in the variable list to be selected. The significance levels for entry (SLE) and significance levels for stay (SLS) were conservatively set to 0.15. Then, with the aid of substantive knowledge, the best candidate final Cox's model was identified manually by dropping the covariates with a p value of >0.05 one at a time until all regression coefficients were significantly different from 0. Any discrepancy between the results of the univariate and multivariate analyses was likely to be due to the confounding effects of uncontrolled covariates in the univariate analysis or the masking effects of intermediate variables in the multivariate analysis.

The GOF measures, concordance, and adjusted generalized $R^2$ were examined to assess the COF of the fitted Cox's model. The concordance, which is a value between 0 and 1, of the Cox's model is equivalent to the c statistic of the logistic regression model; thus, its value of ≥0.7 suggests an acceptable discriminative power. However, the values of the adjusted generalized $R^2$ ($0 \le R^2 \le 1$), proposed by Nagelkerke (1991), are usually low for the Cox's model; in our experience, adjusted generalized $R^2 \ge 0.15$ indicates an acceptable fit for the Cox's model.

Simple and multiple generalized additive models (GAMs) were fitted to draw GAM plots for detecting the nonlinear effects of continuous covariates and then identifying appropriate cutoff point(s) for discretizing continuous covariates, if necessary, during the stepwise variable selection procedure. Computationally, the vgam function (with the default values of smoothing parameters) of the VGAM package could be used to fit GAMs of continuous, binary, and count responses in R. Because GAMs were originally developed for smoothing the effects of continuous covariates in generalized linear models (GLMs), we fitted the GAMs of a binary response (i.e., 1=recurrence or death vs. 0=censored) for DFS to the long-form PP data and used the plot function to plot the smoothed effects of continuous covariates (called the "GAM plot") for visual examination. Moreover, we specified the smoothing option pspline (for the "smoothing splines using a p-spline basis") inside the coxph function of the survival package to smooth the effects of continuous covariates on the DFS of simple and multiple Cox's models and used the termplot function to plot the smoothed effects of continuous covariates (called the "p-spline plot") for visual examinations in R (Moore, 2016, pp. 84-85). In particular, we performed GAM and p-spline smoothing analyses separately in the three subgroups of patients, namely (1) those with macrovascular invasion, (2) those with microvascular invasion, and (3) those without vascular invasion, to detect the heterogeneous nonlinear effects of continuous covariates (e.g., size of the largest tumor) in these subgroups. Finally, the statistical tools of regression diagnostics for residual analysis, detection of influential cases, and multicollinearity assessment were applied to discover any model or data problems. Values of variance inflating factor (VIF)≥10 in continuous covariates or VIF≥2.5 in categorical covariates indicate the occurrence of the multicollinearity problem among some of the covariates in the fitted Cox's model.

The anti-HBV drug is selected from the group consisting of Adefovir, Adefovir Dipivoxil, Entecavir, Lamivudine, Telbivudine, Tenofovir, and Tenofovir Disoproxil Fumarate The anti-HCV drug is selected from the group consisting of Ribavirin, Peginterferon, Peginterferon alfa-2A, Peginterferon alfa-2B, and Pegylated Interferon alfa-2A, Paritaprevir, Simepravir, CGrazoprevir, Ladispavir, Ombitasvir, Elbasavir, Sofosbuvir, Edipasvir, Viekira Pak, Ritonavir and Daclatasvir.

Results

Of the 727 screened patients with hepatitis virus-related HCC after surgical resection, 520 were randomized. The study investigators in this multinational, phase III RCT comprised up to 138 physicians and surgeons specialized in HCC from Taiwan, South Korea, Hong Kong, and China working in a cohort to conduct the trial. This RCT was terminated early in January 2015 because the negative stop boundary was reached in the scheduled interim analysis of Jul. 27, 2014. However, all the study patients had already received treatments at that time, either PI-88 or placebo, for the maximum period of 12 months. Hence, the number of the patients for safety assessment and ITT efficacy analysis still reached the original goals of 518 and 519, respectively (FIG. 1).

Efficacy Analysis

A. ITT Analysis

Figure 2A:
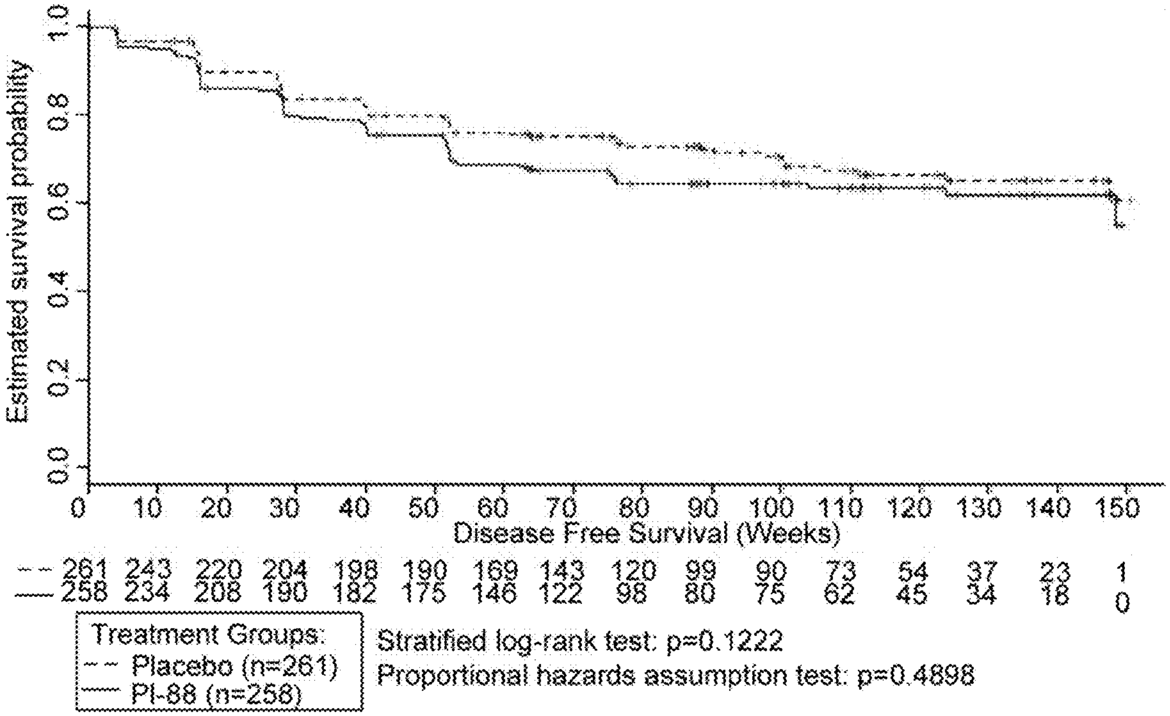
FIGS. 2A-B are graphs showing Kaplan-Meier estimates of disease-free survival curves in the intention-to-treat analysis based on (FIG. 2A) independent central imaging assessments and (FIG. 2B) local imaging assessments at each study site, respectively.
Figure 2B:
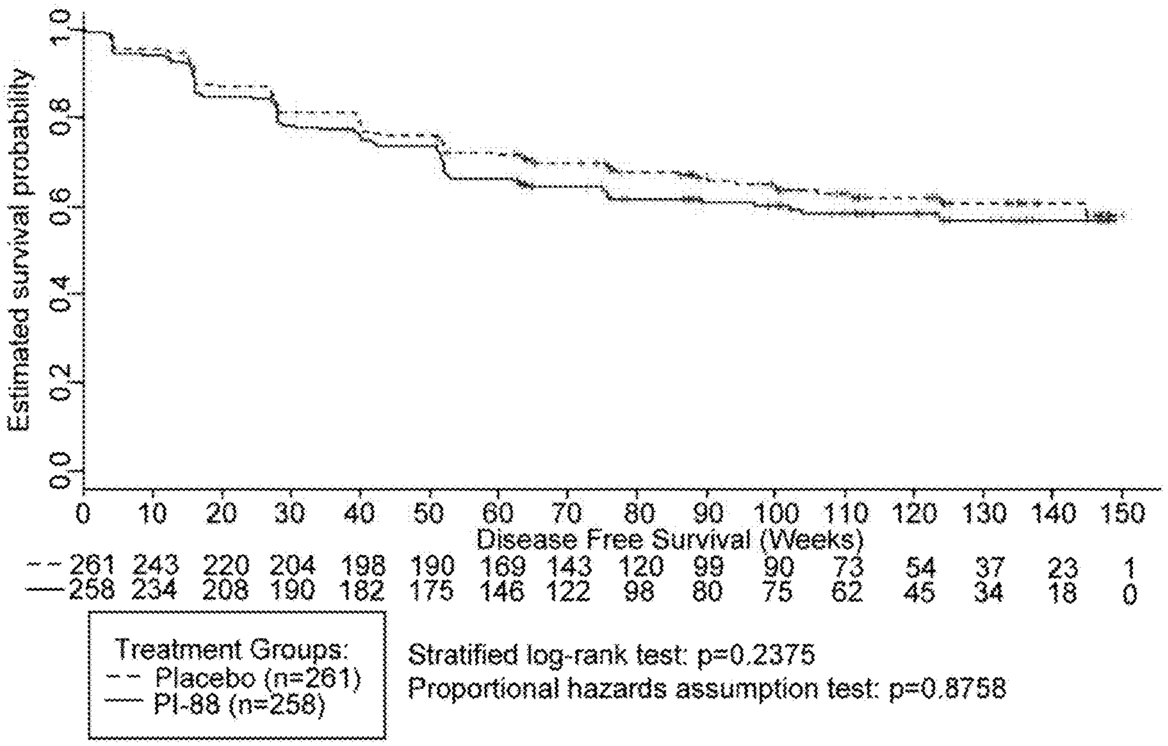
Figure 3A:
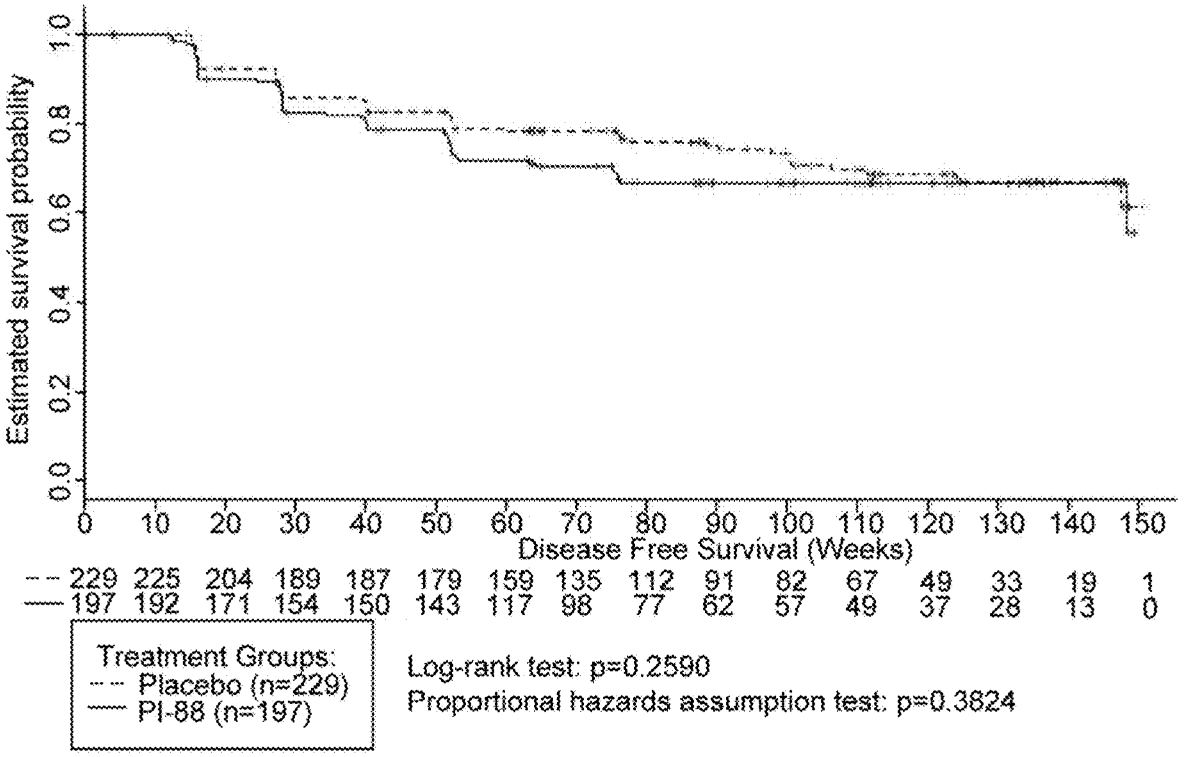
FIGS. 3A-D are graphs showing Kaplan-Meier estimates of disease-free survival curves for (FIG. 3A) all patients and patients with (FIG. 3B) macrovascular invasion.
Figure 3B:
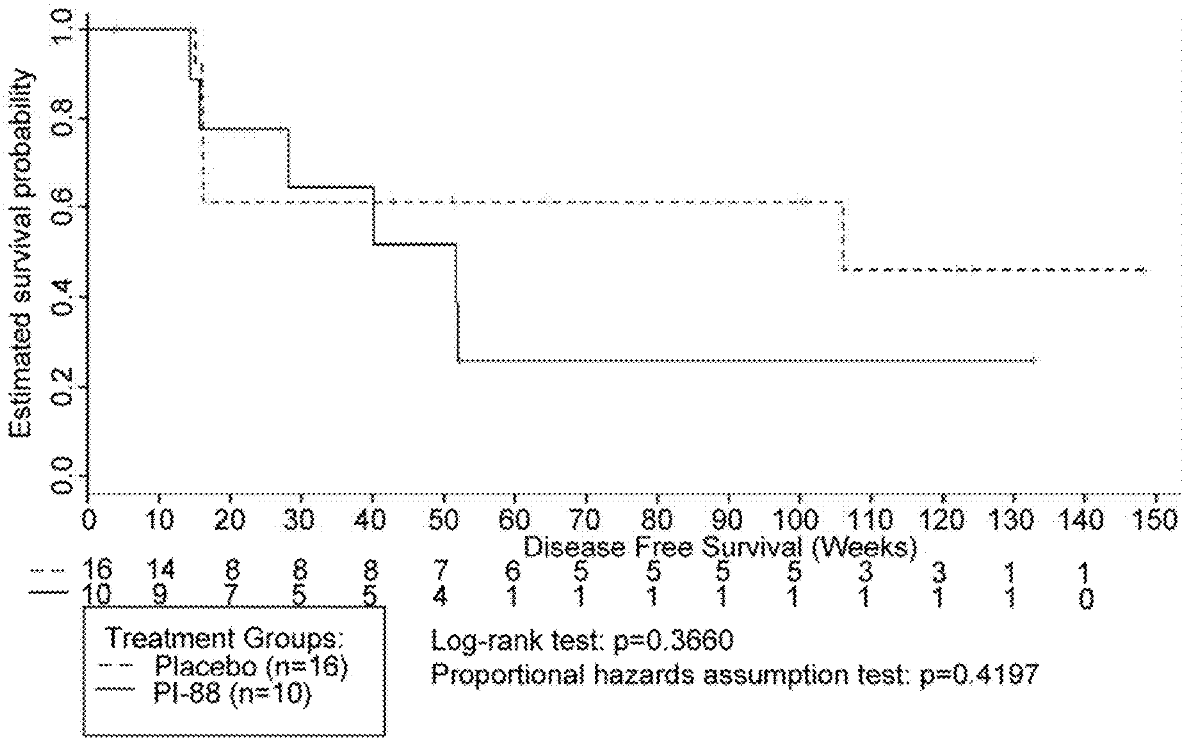
Figure 3C:
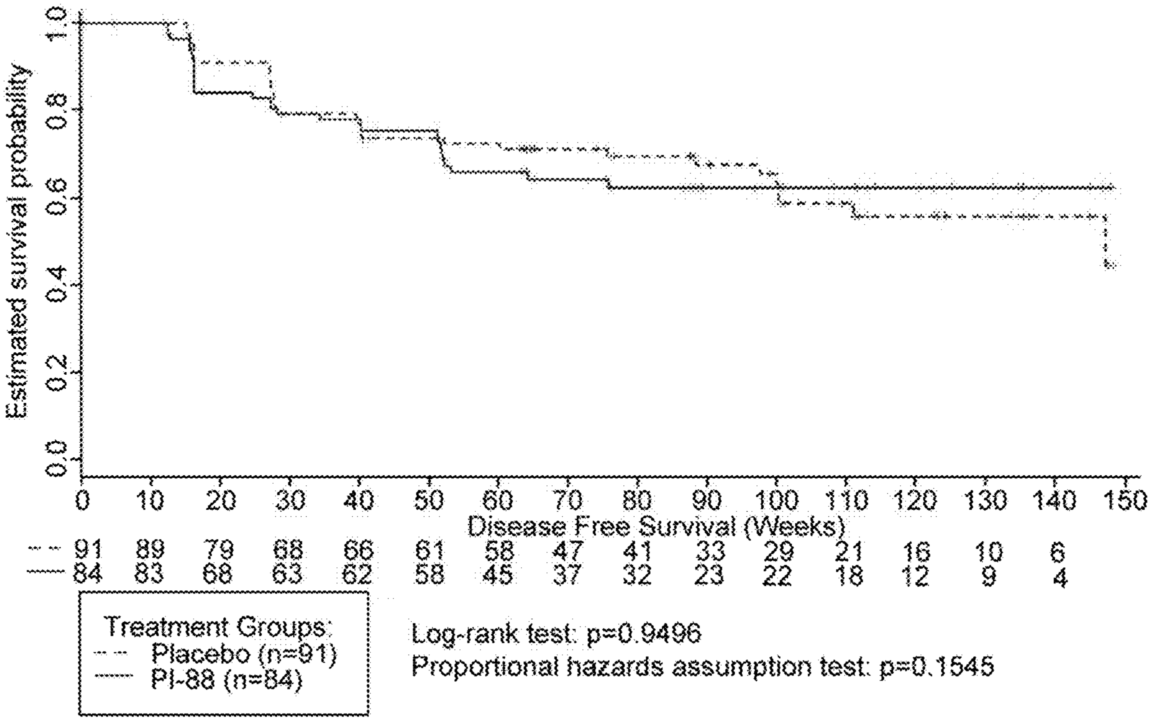
Figure 3D:
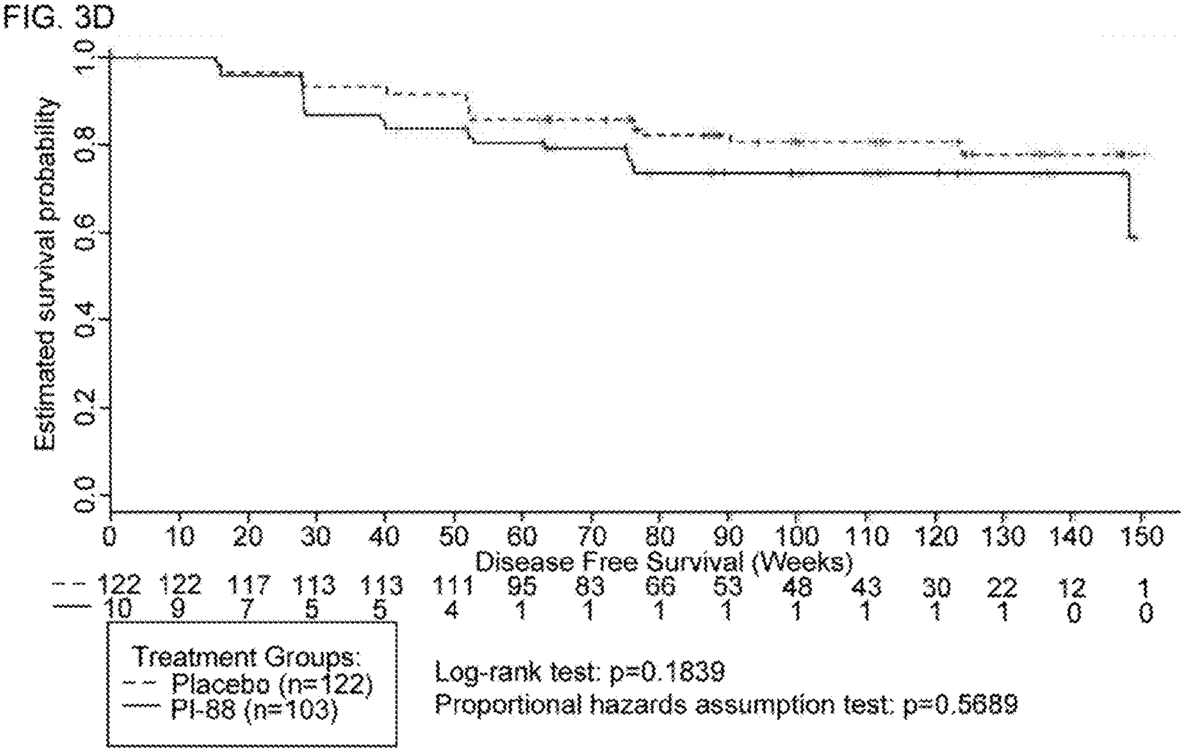

A total of 159 central imaging readings confirmed events amenable to ITT efficacy assessment. Of those, 85 and 74 were in the PI-88 and placebo groups, respectively. As listed in Table 1 (FIG. 6-1 to 6-3), the baseline demographic and clinical characteristics were all balanced between the treatment and placebo arms in the ITT population (n=519). The survival curves of DFS between the PI-88 and placebo groups were compared without statistical significance (p=0.12). The results of Cox's proportional hazards analysis for ITT event assessment showed that the DFS period did not significantly differ between the PI-88 and placebo groups (estimated hazard ratio [HR]: 1.26, 95% confidence interval [CI]: 0.92-1.72, p=0.15, FIG. 2A). A similar Kaplan-Meier DFS curve based on local imaging assessment at study sites is illustrated in FIG. 2B.

In this trial, the time to recurrence was the same as the DFS period because no patients died without a preceding tumor recurrence. Regarding OS, seven deaths were reported, including three in the PI-88 group and four in the placebo group. Median OS was not reached in either treatment group. No significant treatment effect of PI-88 on OS was observed.

B. PP Analysis

A total of 426 patients were eligible for PP analysis. The results of the univariate analyses of treatment groups listed in Table 2 (FIG. 7-1 to 7-3) confirm the comparability of baseline demographic and clinical characteristics between the patients receiving placebo (n=229, 53.76%) and those receiving PI-88 (n=197, 46.24%) in the PP data (n=426). The Kaplan-Meier estimates of survival curves for the two groups are plotted in FIG. 3A. The results of the univariate analyses of vascular invasion subgroups revealed incomparability in many baseline demographic and clinical characteristics among the patients with macrovascular invasion (n=26, 6.10%), microvascular invasion (n=175, 41.08%), and no vascular invasion (n=225, 52.82%) in the PP data (n=426). In addition, the Kaplan-Meier estimates of survival curves for the two groups, placebo and PI-88, with (1) macrovascular invasion, (2) microvascular invasion, or (3) no vascular invasion are plotted in FIGS. 3B, 3C, and 3D respectively. The relatively flat survival curve of the patients receiving PI-88 after the study period of 60 weeks (FIG. 3C) suggested that PI-88 had an unusual "latency effect" on the DFS of the patients with microvascular invasion.

As shown in Table 3 (FIG. 8), multivariate analysis was conducted by fitting Cox's model of DFS, in which the adjusted effects of demographic characteristics, clinical HCC features, time-varying anti-HBV drug use, time-varying anti-HCV drug use, and time-varying PI-88 use on DFS were examined carefully. After adjusting for the effects of other covariates in the fitted Cox's model of DFS, the patients receiving PI-88 whose accumulative time since the end of the last cycle of PI-88 was >16 weeks had 87.22% lower risk of recurrence or death (FIR=0.1278, 95% CI: 0.0168-0.9727, p=0.0470) than did those receiving the placebo in the microvascular invasion subgroup.

Figure 4A:
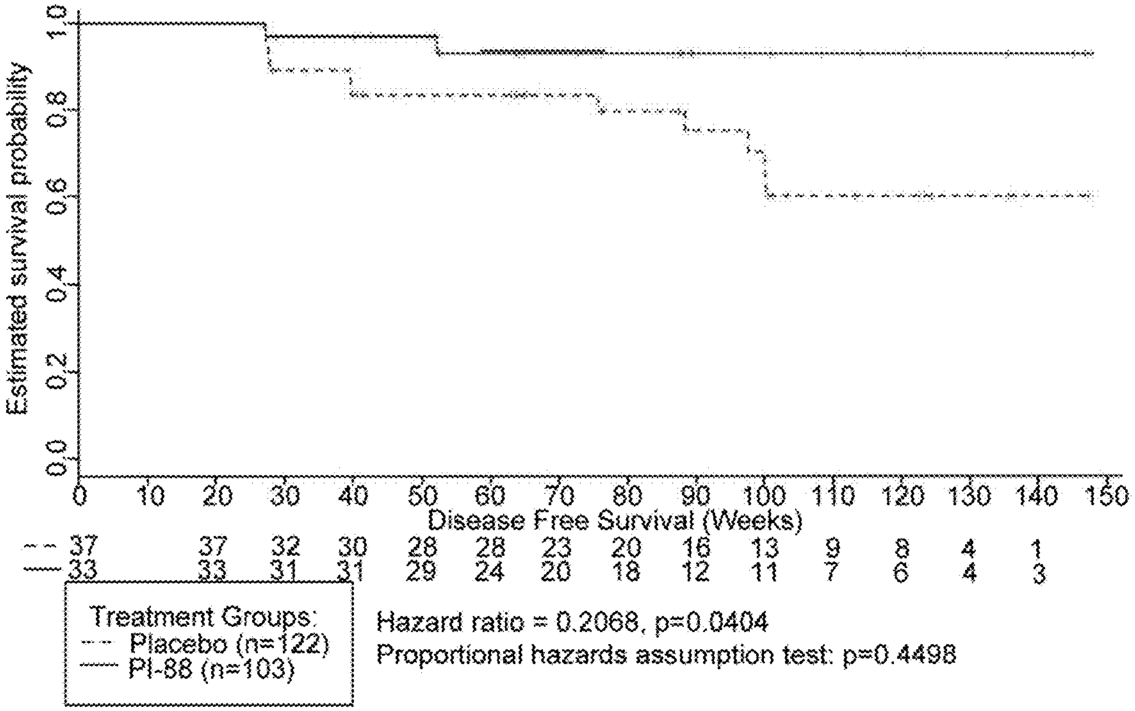
FIGS. 4A-C are graphs showing Kaplan-Meier estimates of disease-free survival curves for "preferable" patients with (FIG. 4A) microvascular invasion.
Figure 4B:
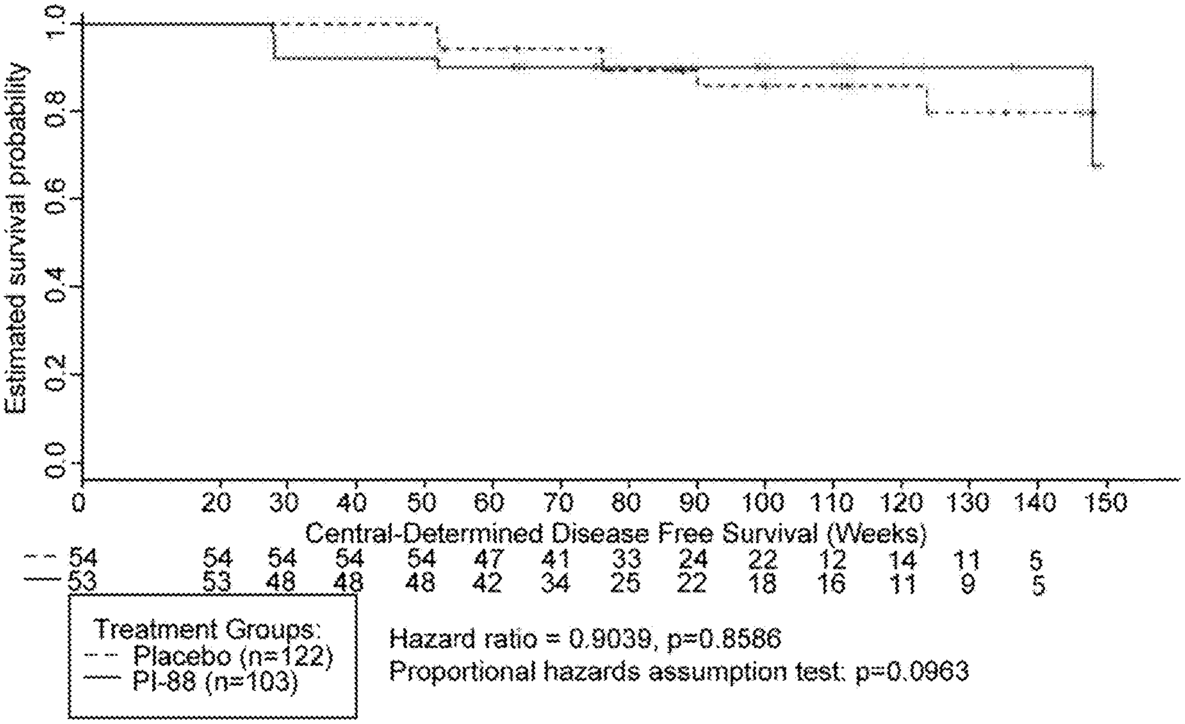
Figure 4C:
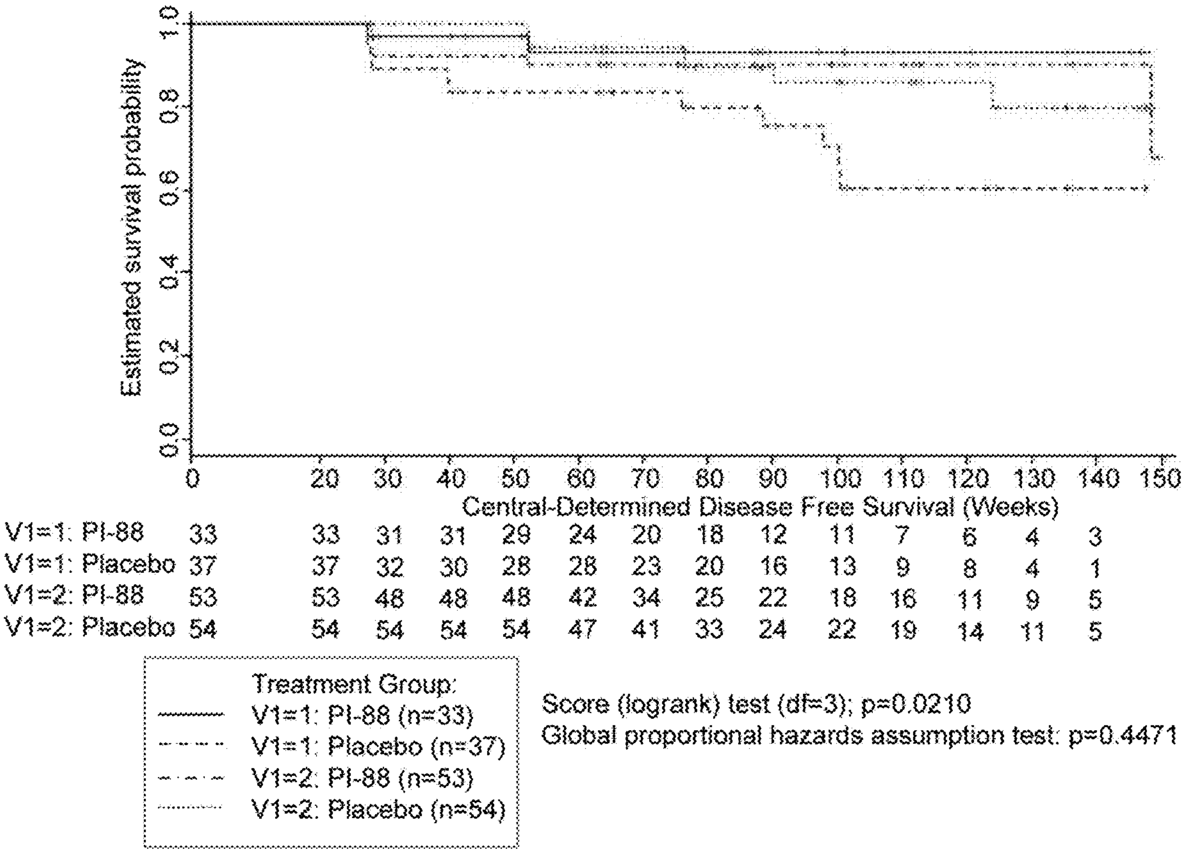

FIG. 4A illustrates the DFS curves of the patients with microvascular invasion whose time to tumor recurrence or death was >24 weeks adjusted for number of tumors, pathological differentiation, Child-Pugh score, macrovascular invasion, tumor size, and anti-HBV or anti-HCV drug use after randomization. The status event is defined as tumor recurrence or death due to any cause; the time is defined from randomization to tumor recurrence or death due to any cause during the study period in weeks; and the arm is either PI-88 or placebo. PI-88 exerted a significant protective effect against tumor recurrence after completing the 1-year treatment (HR=0.2068, p=0.0404). FIG. 4B demonstrates a similar Kaplan-Meier curve for the patients without vascular invasion who received PI-88. In FIG. 4C, FIGS. 4A and 4B are superimposed in the same X and Y scales for easy comparison.

Figure 5:
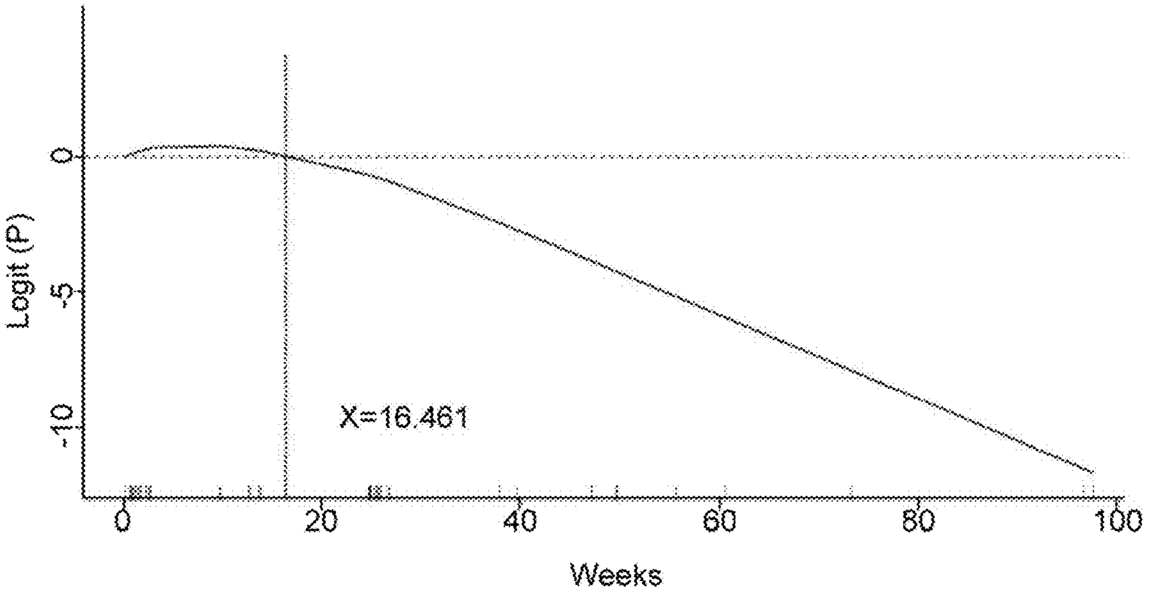
FIG. 5 is a graph showing strong protective effect of muparfostat (PI-88) in a subgroup of patients with microvascular invasion after the study drug had been administered for a period of 52 weeks.

FIG. 5 shows strong protective effect of muparfostat (PI-88) in a subgroup of patients with microvascular invasion after the study drug had been administered for a period of 52 weeks. The unit of X axis is time in weeks. The number on the X axis stands for the "accumulative time (in weeks) since the end of last cycle of Muparfostat in patients with microvascular invasion." For Y axis, P is the probability of tumor recurrence or death, and Logit(P)=log [P/(1−P)]. The number of observations was 16536, which was reconstructed from the original PP data using counting process style of input. For patients with microvascular invasion, 16.461 weeks after the end of last cycle of Muparfostat treatment, the probability of tumor recurrence or death was lower than the probability without tumor recurrence or death. In other words, the ratio of probability of tumor recurrence or death to the probability without tumor recurrence or death declines with time (accumulative weeks since the end of last cycle of Muparfostat).

Safety Profiles

A total of 518 patients received at least one dose of PI-88 (n=258) or placebo (n=260). At the end of the trial, 346 patients completed the treatment at the last cycle (i.e., Cycle 13). More patients in the placebo group (187/260, 71.9%) completed the study treatment at Cycle 13 than those the PI-88 group (159/258, 61.6%). The mean treatment duration in the placebo group (42.16 weeks) was significantly higher than that in the PI-88 group (38.57 weeks, p=0.0210). Treatment compliance (≥80%) was 96.2% (250/260) in the placebo group and 88.8% in the PI-88 group (229/258).

As listed in Table 4 (FIG. 9-1 to 9-2), 152 (58.9%) patients in the PI-88 group and 51 (19.6%) patients in the placebo group reported at least one adverse event (AE), which was considered to be relevant to the study treatment. According to the System Organ Class, treatment-related AEs with the highest incidence were mostly related to general disorders and administration site conditions (PI-88: 31.4%, placebo: 4.6%), and all were mild or moderate in severity. The treatment-related AE with the highest overall incidence was alopecia, which was reported in 58 (22.5%) patients in the PI-88 group and 4 (1.5%) patients in the placebo group, followed by a decreased platelet count, which was reported in 36 (14.0%) patients in the PI-88 group and 10 (3.8%) patients in the placebo group, and injection site hematoma, which was observed in 33 (12.8%) patients in the PI-88 group and 7 (2.7%) patients in the placebo group.

No patients in either study group experienced fatal AEs during the study treatment period. However, seven patients died during follow-up visits. Of these, three patients were in the PI-88 treatment group and four patients were in the placebo group. The causes of death of all the seven patients were confirmed as related to tumor recurrence but not study treatment.

Thirty (11.6%) patients reported 34 treatment emergent serious adverse events (SAEs), but only two were possibly drug related. Of these, 15 (5.8%) patients who experienced 15 treatment emergent SAEs were from the placebo group, and no newly observed safety signals were raised in the study compared with those in earlier trials. Two patients in the PI-88 treatment group experienced treatment-related SAEs. One patient had one event of grade 3 acute myocardial infarction, and another patient had an event of grade 3 dysarthria, both of which were regarded as possibly related to the study drug.

A higher proportion of the PI-88-treated patients (13/258, 5.0%) experienced AEs of Grade 3 or 4, such as a decrease in the platelet count, compared with the placebo-treated patients (7/260, 2.7%). There were five clinically suspected cases of HIT, but only one was considered to be similar to HIT but without a final proof.

In conclusion, the current trial investigated the clinical efficacy of PI-88 as an adjuvant after the curative resection of HCC and evaluated whether this regimen can reduce tumor recurrence after surgery. The results of the ITT-related Kaplan-Meier analysis revealed that DFS did not significantly differ between the placebo and PI-88 groups, either in independent (central) or dependent (local) assessment. The failure of the study to achieve efficacy endpoints might be attributed to the following reasons. First, we made our assumption from previous phase II HCC trials that provided only limited clues to patient selection and clinical efficacy owing to a small sample size. Under such a situation, several critically negative factors, such as macrovascular invasion, large tumor burden (e.g., multiple tumors, tumor size>10 cm, and anaplasia of tumor differentiation), were not excluded or controlled in the trial. Therefore, the recruitment of nonspecific patients in the trial seriously diluted the potential beneficial effects of PI-88 on the study population. Second, the complexity of the HCC tumor microenvironment, which includes cancer cell differentiation, different disease stages, and various heterogeneous hepatocarcinogenesis, may cause diverse effects in the study population. Third, the concomitant use of antiviral nucleoside analogs may overshadow the efficacy of PI-88.

A strong protective effect of PI-88 was found in a subgroup of the patients with microvascular invasion when the study drug was administered for a period of 52 weeks (FIG. 5). This finding suggests that PI-88 provides clinical benefits by modulating the tumor microenvironment to a stable state and that intrahepatic tumor recurrence can be substantially reduced if the drug is administered for a long period.

As the standard care of ICC after surgical resection, the use of anti-IHBV drugs was encouraged in our study for patients with detectable HBV viral load. FIG. 10 shows delayed protective effect of anti-HBV drug in a subgroup of patients without vascular invasion after the drug had been administered for a period of 60 weeks. The unit of X axis is time in weeks. The number on the X axis stands for the "accumulated weeks of anti-HBV drug treatment after randomization minus 28 days prior to each event time", which is defined as accumulative drug days in weeks since the first day of taking the drug after randomization up to each unique event time of DFS, but ignoring the drug usage within the pre-specified time lag of 28 days as the "latency period" or "incubation period" of anti-HBV drug prior to each unique event time of DFS. For Y axis, P is the probability of tumor recurrence or death, and Logit(P)=log [P/(1−P)]. The number of observations was 16536, which was reconstructed from the original PP data using counting process style of input.

For patients without vascular invasion, 61.22 weeks of anti-HBV drug treatment after randomization minus 28 days prior to each event time, the probability of tumor recurrence or death was lower than the probability without tumor recurrence or death. In other words, the ratio of probability of tumor recurrence or death to the probability without tumor recurrence or death declines with time (accumulated weeks of anti-HBV drug treatment after randomization minus 28 days prior to each event time).

As shown in Table 3, anti-HBV drugs have a protective effect on tumor recurrence if used for a long period (e.g., >60 weeks); however, anti-HBV drugs primarily exerts effects on patients without vascular invasion. Studies have suggested that anti-HBV treatment, particularly nucleotide analogs, can reduce the risk of tumor recurrence after curative treatment in patients with HBV-related HCC. However, the results of this study indicated that the protective effect was exerted on only a specific subgroup of the patients without vascular invasion, and the protective power of anti-HBV drugs is lower than that of PI-88.

In the present invention, a Cox's proportional hazards model with time-dependent covariates (i.e., Cox's model) was used to further investigate the effects of the treatment on the patients with microvascular invasion. The results revealed that PI-88 appeared to start exerting its protective effects on recurrence late in the course of the treatment. FIG. 4A depicts a positive PI-88 protective effect in a subset of the patients with microvascular invasion who received the treatment for more than 52 weeks (HR=0.2068). According to the findings of FIGS. 3C-D, and 4B, there was almost no recurrence in the PI-88 study group after 75 weeks. This result strongly demonstrated that PI-88 possesses an undefined biochemical or immunological mode of action other than the already known heparanase inhibition and antiangiogenesis effects. PI-88 exerts unexpected modulatory effects on tumor microenvironment, which are likely to play an enhancing role along with immune checkpoint inhibitor (ICI) effects for various cancer treatments. Thus, PI-88 in combination with immune checkpoint inhibitor (ICI) may have promising potential in cancer therapies.

In the trial, most (>37%) tumor recurrences occurred within 6 months after surgery. Early recurrence within 24 weeks might be due to residual micrometastasis or satellite metastasis after surgical resection. If early recurrences were deliberately excluded from the analysis together with other controlled covariates, the Kaplan-Meier survival curve of the remaining patients would have become more favorable toward the PI-88 group (FIG. 4A). PI-88 is an agent that has a cytostatic, but not cytotoxic, mechanism of action, and it is unreasonable to expect that small cancer foci already existing in the liver, which are invisible in imaging or undetectable by biochemistry tests, can be unanimously eradicated by PI-88 if they are left over in the liver tissue after surgery. These minute HCC residuals may become the foci of secondary growth soon after surgery because partial hepatectomy per se may play a crucial role in accelerating the carcinogenesis of HCC. The inability to suppress the growth of remaining cancer foci within the liver post surgery is probably one of the reasons why PI-88 failed to demonstrate a benefit in DFS in this study. However, it is encouraging to find that in the trial, the overall 1-, 2-, and 3-year DFS rates were 73%, 66%, and 58%, respectively, which are comparable to survival outcomes reported in most other HCC meta-analyses to date.

In the present invention, most recurrences occurred early after surgery. Because such results have a significant impact on DFS analyses, it inevitably creates a risky hurdle for any clinical study to validate the efficacy of an adjuvant therapy for patients with HCC after surgery. Although HCC surgery with curative intent aims at the total removal of all cancer foci in the liver, it only can resect the technically and radiologically detectable and technically feasible cancer foci. The invisible or undetectable microcluster of cancer cells may have already spread outside the main tumors undergoing resection.

The discovery of the present invention are as follows. First, microenvironment-modifying agents, such as PI-88, might only work for minimal residual tumors after surgery; thus, careful selection of patients to better suit this criterion is critical. Second, a more precise clarification of recurrence may be required to separate the recurrence secondary to residual cancer foci after curative surgery from the recurrence that is non-existing at the time of surgery but arise elsewhere independent of the primary tumor (de novo). Third, there should be a reasonable scheme to exclude early recurrence (e.g., recurrence within 6 months) after surgery because those recurrence may be more relevant to surgical outcomes than to drug effects per se.

In conclusion, although DFS was not improved in the whole PI-88 treatment group, PI-88 could significantly prolong the DFS period in the subgroup of patients with microvascular invasion in the histology of resected samples (accounted for nearly 40% of the treated population). In this group of patients, if PI-88 was administered for a prolonged time period (e.g., >52 weeks), the tumor recurrence protecting effect became significant. On the other hand, the DFS period in the subgroup of patients without vascular invasion in the histology of resected samples (accounted for more than 50% of the treated population) could be prolonged by administering an anti-HBV drug for a time period (e.g., >60 weeks). However, for the subgroup of patients with macrovascular invasion in the histology of resected samples (accounted for less than 10% of the treated population), neither PI-88 nor anti-HBV drugs could prolong the DFS period significantly. To sum up, the present invention showed that the characterization of vascular invasion of HCC patients is not only meaningful in prognosis but also crucial for selecting the effective medication to prolong patients' life expectancy after liver resection.

Additionally, with the recent increasing knowledge of heparanase and other growth factors that play roles in tumor microenvironment modulations, the present invention also indicated the potential of PI-88 as a single therapy or in combination with other anticancer agents for future HCC trials.

The foregoing description of the exemplary embodiments of the invention has been presented only for the purposes of illustration and description and is not intended to be exhaustive or to limit the invention to the precise forms disclosed. Many modifications and variations are possible in light of the above teaching.

Alternative embodiments will become apparent to those skilled in the art to which the present invention pertains without departing from its spirit and scope. Accordingly, the scope of the present invention is defined by the appended claims rather than the foregoing description and the exemplary embodiments described therein. Some references, which may include patents, patent applications and various publications, are cited and discussed in the description of this invention. All references cited and discussed in this specification are incorporated herein by reference in their entireties and to the same extent as if each reference was individually incorporated by reference.

What is claimed is:

1. A method for reducing intrahepatic tumor recurrence and increasing disease-free survival period of a hepatocellular carcinoma (HCC) patient, the method comprising:

administering a therapeutically effective amount of muparfostat to the HCC patient after curative liver resection, wherein the patient microvascular invasion but does not have macrovascular invasion, and wherein the muparfostat is administered to the patient for at least about 52 weeks.

2. The method of claim 1, the method further comprising: prior to the administering step, examining a resected liver tumor sample from the patient to identify presence of the microvascular invasion in the sample.

3. The method of claim 1, wherein the patient is non-responsive to anti-hepatitis B virus drug treatment.

4. The method of claim 1, the method further comprising administering a therapeutically effective amount of an immune checkpoint inhibitor to the patient.

5. The method of claim 1, the method further comprising administering an additional anticancer agent to the patient.

6. The method of claim 1, wherein muparfostat is the only anticancer agent received by the patient.

7. The method of claim 1, wherein the patient has one and no more than one single tumor prior to the liver resection.

8. The method of claim 1, wherein the patient has a postoperative Child-Pugh total score of lower than 8.

9. The method of claim 1, the method further comprising: performing surveillance CT scans on the patient every three months.

10. The method of claim 1, wherein the patient does not have an anaplasia hepatic tumor prior to the liver resection.

11. The method of claim 1, wherein the patient has a body mass index (BMI) of 18.5 $kg/m^2$ to 35 $kg/m^2$.

12. A method for treating a hepatocellular carcinoma (HCC) patient after liver resection, said method comprising:

administering a therapeutically effective amount of muparfostat to the patient for at least about 52 weeks, wherein the patient microvascular invasion but does not have macrovascular invasion and hepatitis B virus (HBV) infection or hepatitis C virus (HCV) infection.

13. The method of claim 12, the method further comprising:

prior to administering the muparfostat, assessing whether a liver tumor sample from the patient has the microvascular invasion.

14. The method of claim 1, wherein the patient has hepatitis B virus (HBV)-related HCC or hepatitis C virus (HCV)-related HCC.

15. The method of claim 1, wherein the administering step is performed for at least four consecutive days per week for 3 weeks out of every 4 weeks.

16. The method of claim 1, wherein administering the muparfostat comprises administering the muparfostat to the patient for the first time at, least about 5.2 weeks after performing the liver resection.

17. A method for treating a hepatocellular carcinoma (HCC) patient after liver resection, the method comprising:

administering a therapeutically effective amount of muparfostat to the patient after the liver resection for at least about 52 weeks;

wherein the patient has microvascular invasion but does not have macrovascular.

18. The method of claim 17, wherein the patient has one and no more than one single pre-resection tumor with a size of greater than or equal to about 2 cm and less than about 10 cm, or greater than or equal to about 2 cm and less than or equal to about 5 cm.

19. The method of claim 17, wherein the patient has hepatitis B virus (HBV)-related HCC or hepatitis C virus (HCV)-related HCC.

20. The method of claim 7, wherein the size of the tumor is greater than or equal to about 2 cm and less than about 10 cm, or greater than or equal to about 2 cm and less than or equal to about 5 cm.

21. The method of claim 1, wherein the probability of intrahepatic tumor recurrence decreases with time after treatment.

22. The method of claim 12, wherein the probability of HCC recurrence decreases with time after treatment.

23. The method of claim 17, wherein the probability of HCC recurrence decreases with time after treatment.

24. The method of claim 1, wherein the muparfostat is administered to the patient for about 52 weeks.

25. The method of claim 12, wherein the muparfostat is administered to the patient for about 52 weeks.

26. The method of claim 17, wherein the muparfostat is administered to the patient for about 52 weeks.

* * * * *